(12) United States Patent
Pitman et al.

(10) Patent No.: US 7,356,415 B1
(45) Date of Patent: Apr. 8, 2008

(54) SIMILARITY SEARCHING OF MOLECULES BASED UPON DESCRIPTOR VECTORS CHARACTERIZING MOLECULAR REGIONS

(75) Inventors: Michael C. Pitman, Pine Bush, NY (US); Daniel E. Platt, Bedford Hills, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/275,568

(22) Filed: Mar. 24, 1999

(51) Int. Cl.
 *G01N 33/48* (2006.01)
(52) U.S. Cl. ...................................................... 702/19
(58) Field of Classification Search ................. 702/12; 703/19, 22
See application file for complete search history.

(56) References Cited

U.S. PATENT DOCUMENTS

| | | | |
|---|---|---|---|
| 5,025,388 A | 6/1991 | Cramer et al. ............. | 364/496 |
| 5,784,294 A | 7/1998 | Platt et al. ................. | 364/496 |

OTHER PUBLICATIONS

Ramakrishnan R., Database Management Systems, WCB/McGraw-Hill, 1998. (pp. 28, 29, 57-59, and 72 provided).*
Perkins et al., "Molecular surface-volume and property matching to superpose flexible dissimilar molecules." J. Comput.-Aided Mol. Des. 1992, vol. 6, pp. 475-486.
Willet et al., "Similarity Searching in Files of Three-Dimensional Chemical Structures: Flexible Field-Based Searching of Molecular Electrostatic Potentials." J. Chem. Inf. Compt. Sci. 1996, vol. 36, pp. 900-908.
Gerhard Klebe, "Structural Alignment of Molecules." Klebe, G., Structural Alignment of Molecules, in 3D QSAR in Drug Design. Theory, Methods and Practice. pp. 173-199.
Press et al., "Numerical Recipes." Cambridge University Press, 1986, pp. 349-363.
Richard D. Cramer et al., Comparative Molecular Field Analysis (CoMFA). 1. Effect of Shape on Binding of Steroids to Carrier Proteins. J.Am. Chem. Soc. vol. 110. 1988, pp. 5959-5967.
Andrew C. Good et al., "Structure-Activity Relationships from Molecular Similarity Matrices." J.Med. Chem., vol. 36, 1993, pp. 433-438.
Ajay N. Jain et al., "Predicting Biological Activities from Molecular Surface Properties. Performance Comparisons on a Steroid Benchmark." J. Med. Chem., vol. 37, 1994, pp. 2315-2327.

(Continued)

*Primary Examiner*—Cheyne D Ly
(74) *Attorney, Agent, or Firm*—Michael J. Buchenhorner; Vazken Alexanian

(57) ABSTRACT

A method in a data processing system for generating and storing in a database at least one descriptor vector and at least one reference frame for at least one region of a molecule includes a step of generating an entry including: i) a key derived from the at least one descriptor vector, wherein the key identifies the at least one region, and ii) a set of axes derived from property distribution information of the at least one region, the set of axes characterizing the at least one region. The method further includes steps of applying a mapping to the descriptor vector associated with the at least one region based on preselected criteria and storing the entry in a memory, wherein the key is associated with the entry such that the key indexes the entry for retrieval thereof.

14 Claims, 11 Drawing Sheets

OTHER PUBLICATIONS

William Fisanick et al., "Similarity Searching on CAS Registry Substrances. 1. Global Molecular Property and Generic Atom Triangle Geometric Searching." Journal of Chemical Information & Computer Sciences, vol. 32, No. 6, 1992, pp. 664-674.

William Fisanick et al., "Similarity Searching on CAS Registry Substances 2. 2D Structural Similarity." Journal of Chem Info & Computer Sciences, vol. 34, No. 1, 1994, pp. 130-140.

Ken Turkowski, "The Use of Coordinate Frames in Computer Graphics." Academic Press, edited by A. Glassner, pp. 522-532.

Michael L. Connolly, "Computation of Molecular Volume." JACS, vol. 107, 1985, pp. 1118-1124.

Mike Crenshaw Pitman, Fragment Assembly in the Automated Molecular Invention system: Invention by Mike Crenshaw Pitman, 1995, University of California, Santa Cruz. pp. 1-199.

Yvonne C. Martin, "A Fast New Approach to Pharmacophore Mapping and its Application to Dopaminergic and Benzodiazepine Agonists", J. Comput.-Aided Molecular Design, 1992, vol. 6, pp. 83-102.

* cited by examiner

FIG. 4

GROUP

|   | 1 | 2 | 3 | 4 | · · · | N |
|---|---|---|---|---|-------|---|
| 1 |   |   |   |   |       |   |
| 2 |   |   |   |   |       |   |
| 3 |   |   |   |   |       |   |
| 4 |   |   |   |   |       |   |
| ⋮ |   |   |   |   |       |   |
| M |   |   |   |   |       |   |

FACTOR

SIMILARITY SEARCHING OF MOLECULES BASED UPON DESCRIPTOR VECTORS CHARACTERIZING MOLECULAR REGIONS

CROSS-REFERENCE TO RELATED APPLICATIONS

The present application is related to U.S. Pat. No. 6,408,321, entitled "Method and Apparatus for Mapping Components of Descriptor Vectors to a Space That Discriminates Between Groups," and U.S. Pat. No. 6,349,265, entitled "Method and Apparatus for Mapping Components of Descriptor Vectors for Molecular Complexes to a Space That Discriminates Between Groups," which are herein incorporated by reference to their entirety.

BACKGROUND OF THE INVENTION

1. Technical Field

The invention relates to the field of molecular similarity searching, and, more specifically, similarity searching in databases of three dimensional molecular structures.

2. Description of the Related Art

In the field of drug design, where one is attempting to expand the number of lead compounds that show activity toward a particular therapeutic target, structural information about the target is often lacking or unavailable. Similarity searching in files of chemical compounds is a common way to uncover new leads in such situations. Typically, one or more compounds that are known to be active toward the target of interest are selected, and a feature scheme is defined that characterizes the molecular properties of interest. Features are derived from the selected structures and used to search against a database of structures that have been keyed under the same feature scheme.

Feature schemes may be structural (three-dimensional) in nature or topological (derived solely from the molecular graph). Features that are three-dimensional (3D) characterize a whole or part of a particular conformation of a molecule, and thus are dependent on the particular conformations of the molecules stored in the database. 3D features can include a) pharmacophoric descriptors, such as distances, angles, or dihedral angular relationships between key groups (see Martin, Y. et. al., A fast new approach to pharmacophore mapping and its application to dopaminergic and benzodiazepine agonists. J. Comput.-Aided Mol. Des. 1992, Vol 6, pp. 475-486; b) Surfaces characterizations (see Perkins et. al. Molecular surface-volume and property matching to superpose flexible dissimilar molecules. J. Comput.-Aided Mol. Des. 1995, Vol 9, 479-490); or c) Field-based properties that characterize regions of a molecule (see Willet. et. al. in Similarity searching in files of three-dimensional chemical structures: Flexible field-based searching of molecular electrostatic potentials. J. Chem. Inf. Comput. Sci. 1996, Vol 36, pp. 900-908).

Similarity searching for compounds in 3D databases is an important part of lead generation, and is commonly practiced in the drug design process (see Klebe G, Structural Alignment of Molecules, in 3D QSAR in Drug Design. Theory, Methods, and Practace, and Kearsley, S. K. et. al, An alternative method for the alignment of molecular structures: Maximizing electrostatic and steric overlap. Tetrohedron Comput. Methodol. 1990, Vol 3, pp. 615-633). It is useful in expanding the list of active compounds for a therapeutic target, finding new uses for existing compounds, getting around a competitors patent, or gaining more insight into the nature of the therapeutic target under investigation. There are, however, several ways one may conduct such searches, with no one method proven superior or universally applicable. Novel procedures are thus a current research interest.

A common problem that arises in similarity searching is that of preparing an appropriate distance metric. The problem arises when one must decide how to weight the relative importance of descriptors when evaluating whether two features are similar. The problem is compounded by the fact that different contexts warrant different scalings of descriptors. Appropriate distance metrics in one context may not be suitable for another.

The present invention embodies a novel procedure for a 3D similarity searching that is based on the alignment of heuristic property fields. The particular novelty offered by the present invention is the independence of the particular property field used, and a context dependent scaling procedure that allows a training set to scale the descriptors.

SUMMARY OF THE INVENTION

The problems stated above and the related problems of the prior art addressed with the principles of the present invention, similarity searching of molecules based upon statistical analysis of descriptor vectors characterizing molecular regions.

In a training phase, an association criterion is generated by which query regions of a query molecular are associated with regions of molecules stored in a database. Preferably, the association criterion is based upon statistical analysis of groups of descriptor vectors that characterize properties of the regions of the molecules stores in the database.

In an acquisition phase, for each molecule in a series of molecules, the following steps are performed for a given molecule. Data that represents the structure of the given molecule is read from persistent memory and used to define a set of three-dimensional regions of space in the given molecule. For each region, one or properties of the given molecule are mapped to property values for grid points of the region. A multi-map entry is generated that identifies the region, and position and orientation of set of axes derived from the property values of the grid points of the region. The association criterion generated in the training phase is used generate a key for the region, and the entry is stored in the multi-map at a location associated with the key.

In the recognition phase, data that represents the structure of a query molecule is used to define a set of regions in the query molecule. For each region, one or properties of the query molecule are mapped to property values for grid points of the query region. The association criterion generated in the training phase is used generate a key for the query region. The multi-map entry identified by the key is retrieved and the data stored therein are read from the table. For each stored region identified by the retrieved table entry, an hypothesized match is constructed and added to a vote table. After processing all of the stored regions identified by the retrieved multi-map entry for the set of query regions in the query molecule, one or more entries of the vote table is selected, the alignment transformations stored in the selected entries are applied to corresponding molecules stored in the database, and the resultant alignment(s) of the stored molecule in the query frame is reported to the user via an I/O device.

BRIEF DESCRIPTION OF THE DRAWINGS

FIG. 4 is a table illustrating a multi-factor design with multi-way analysis of variance.

DETAILED DESCRIPTION OF THE INVENTION

Figure 1A:
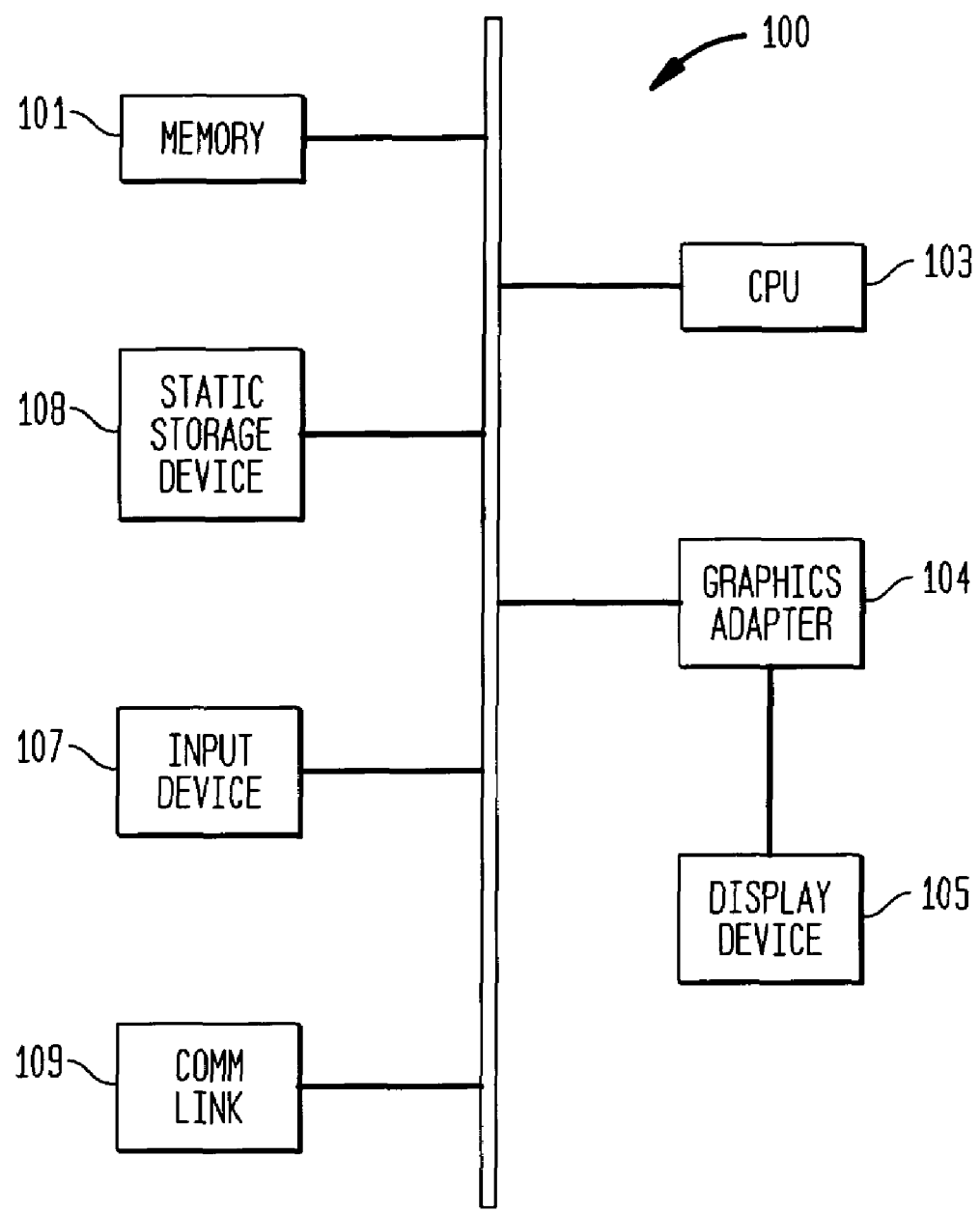
FIGS. 1(A) and 1(B) are block diagrams of computer processing systems wherein the methods of the present invention may be embodied.

The present invention may be implemented on any computer processing system including, for example, a personal computer or a workstation. As shown in FIG. 1(A), a computer processing system 100 as may be utilized by the present invention generally comprises memory 101, at least one central processing unit (CPU) 103 (one shown), and at least one input device 107 (such as a keyboard, mouse, joystick, voice recognition system, or handwriting recognition system). In addition, the computer processing system includes a nonvolatile storage device 108, such as a ROM or fixed disk drive, that stores an operating system and one or more application programs that are loaded into the memory 101 and executed by the CPU 103. In the execution of the operating system and application program(s), the CPU may use data stored in the nonvolatile storage device 108 and/or memory 101. In addition, the computer processing system includes a graphics adapter 104 coupled between the CPU 103 and a display device 105 such as a CRT display or LCD display. In addition, the computer processing system may include a communication link 109 (such as a network adapter, RF link, or modem) coupled to the CPU 103 that allows the CPU 103 to communicate with other computer processing systems over the communication link, for example over the Internet. The CPU 103 may receive portions of the operating system, portions of the application program(s), or portions of the data used by the CPU 103 in executing the operating system and application program(s).

It should be noted that the application program(s) executed by the CPU 103 may perform the methods of the present invention described below. Alternatively, portions or all of the methods described below may be embodied in hardware that works in conjunction with the application program executed by the CPU 103.

Figure 2A:
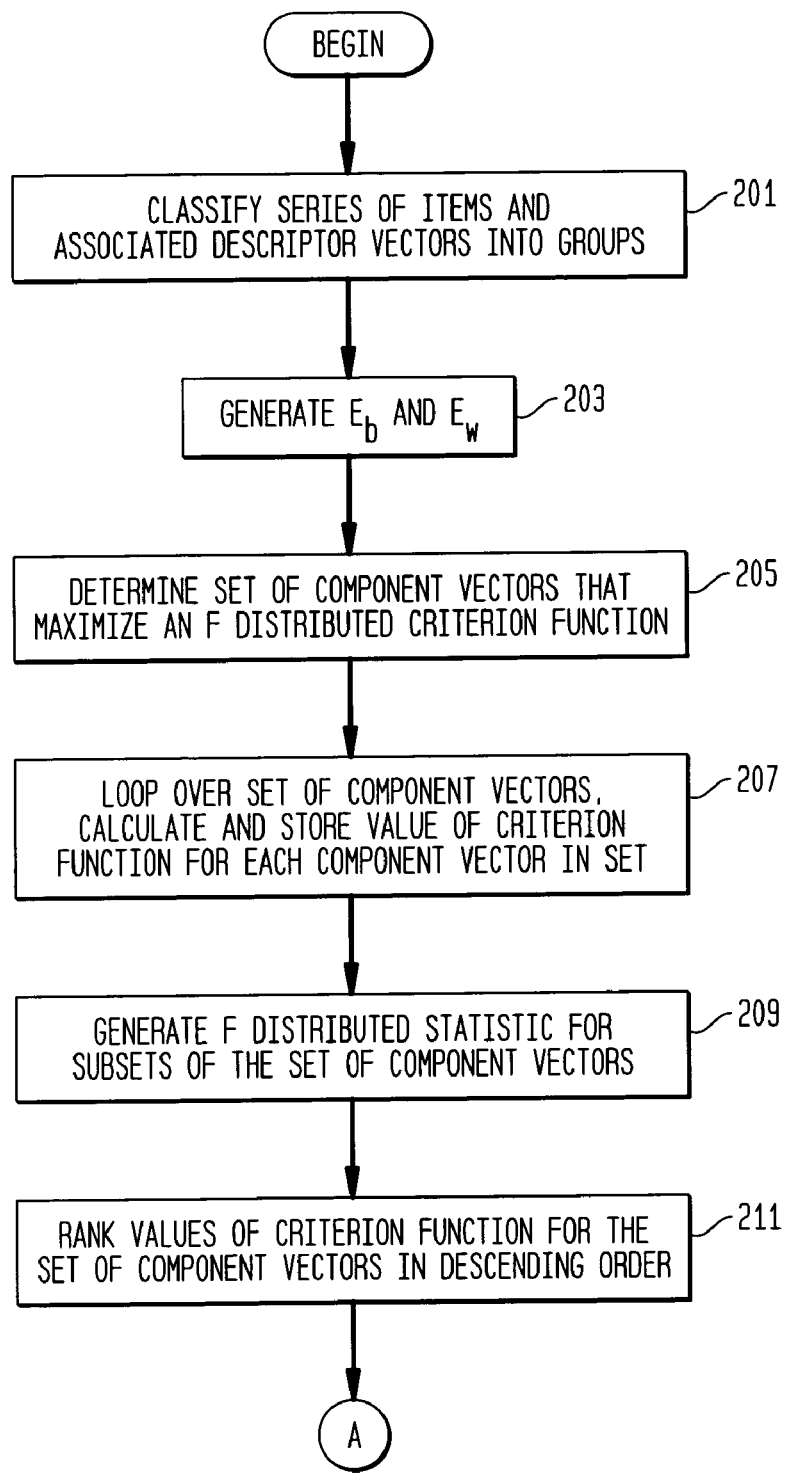
FIGS. 2(A) and (B) is a flow chart illustrating the method of the present invention in mapping a descriptor vector for an item to a space that optimally discriminates between groups of items in accordance with the present invention.

According to the present invention, a computer implemented method provides a mapping (i.e., a transformation) for the components of the descriptor vectors for a series of items to a space that optimally discriminates between groups of items. With reference to FIGS. 2(A) and (B), the operation begins in step 201 wherein a series of items are classified into N groups (N is an integer greater than 1), wherein each group is identified by an identifier i ranging from 1 to N. For the sake of description, consider groups that contain $n_i$ items and descriptor vectors; however, the present invention is not limited in this respect and can be used for groups that contain a non-uniform number of items and descriptor vectors. In addition, $m_{ij}$ identifies item j belonging to group i where j ranges from 1 to $n_i$, and $\vec{x}_{ij}$ is the descriptor vector corresponding to the item $m_{ij}$. Preferably, the descriptor vectors are stored as part of a file in persistent storage and loaded into non-persistent storage for use by the CPU 103 as needed.

In step 203, first data representing covariance between the groups of the items, denoted $\epsilon_b$, are generated. In addition, second data representing covariance within the items belonging to the groups, denoted $\epsilon_w$, are generated. Note that both the first data and second data follow a chi-square distribution. An example of the operations in determining $\epsilon_b$ and $\epsilon_w$ is provided below. In this example, the first data ($\epsilon_b$) have a chi-square distribution with N−1 degrees of freedom (where N represents the number of groups of items); and the second data ($\epsilon_w$) have a chi-square distribution with $\Sigma n_i$−N degrees of freedom (where N represents the number of groups of items, $n_i$ represents the number of items in group i, and $\Sigma n_i$ represents the sum of $n_i$ for the N groups).

An example of the operations in determining $\epsilon_b$ and $\epsilon_w$ is now provided. One may break any given descriptor vector $\vec{x}_{ij}$ into variation between groups and variations within a group as follows:

$$\vec{x}_{ij} = \vec{a} + \vec{a}_i + \vec{a}_{ij},$$

where $\vec{a}$ represents the mean of all the items (of all the groups);

$\vec{a}_i$ represents deviation from mean of all the items ($\vec{a}$) to the mean of groups i; and $\vec{a}_{ij}$ represents deviation from the mean of group i ($\vec{a}_i$) to the descriptor vector $\vec{x}_{ij}$.

For each group of i of items (i.e., i ranging from 1 to N), the sample mean, denoted $\vec{X}_{i.}$, of the descriptor vectors within group i is calculated. For example, the sample mean of the descriptor vectors in a given group i may be calculated as follows:

$$\vec{X}_{i.} = \frac{1}{n_i} \sum \vec{x}_{ij},$$

where the $\Sigma$ operator sums over the range of j=1 to $n_i$

The sample mean $\vec{a}$ of all the items is calculated. For example, the sample mean $\vec{a}$ may be calculated as follows:

$$\vec{a} = \frac{1}{N} \sum \vec{X}_{i.},$$

where the $\Sigma$ operator sums over the range of i=1 to N

For each group i of items (i.e., i ranging from 1 to N), the deviation $\vec{a}_i$ is calculated. For example, the deviation $\vec{a}_i$ for a given group i may be calculated as follows:

$$\vec{a}_i = \vec{X}_{i.} - \vec{a}$$

For each descriptor vector $\vec{x}_{ij}$, the deviation $\vec{a}_{ij}$ is calculated. For example, the deviation $\vec{a}_{ij}$ may be calculated for a given descriptor vector $\vec{x}_{ij}$ as follows:

$$\vec{a}_{ij} = \vec{x}_{ij} - \vec{X}_{i.}$$

The covariance between groups, denoted $\epsilon_b$, may be calculated as follows:

$$\epsilon_b = \Sigma n_i \vec{a}_i \vec{a}_i^T,$$

where the $\Sigma$ operator sums over the range of i=1 to N

And the covariance within groups, denoted $\epsilon_w$, may be calculated as follows:

$$\epsilon_w = \Sigma\Sigma \vec{a}_{ij} \vec{a}_{ij}^T,$$

where the $\Sigma\Sigma$ operator sums over the range j=1 to $n_i$ for each i in the range 1 to N Note that the covariance between groups $\epsilon_b$ has a chi-square distribution with N−1 degrees of freedom (where N represents the number of groups of items); and the covariance within groups $\epsilon_w$ has a chi-square distribution with $\Sigma n_i$−N degrees of freedom (where N represents the number of groups of items, $n_i$ represents the number of items in group i, and $\Sigma n_i$ represents the sum of $n_i$ for the N groups). The total covariance, denoted $\epsilon$, is represented as follows:

$$\epsilon = \Sigma\Sigma(\vec{x}_{ij} - \vec{a})(\vec{x}_{ij} - \vec{a})^T = \epsilon_b + \epsilon_w,$$

where the $\Sigma\Sigma$ operator sums over the range j=1 to $n_i$ for each group i in the range 1 to N In step 205, an F distributed criterion function is used to determine a set of component vectors that maximize the criterion function. The criterion function has a numerator and a denominator, whereby the numerator is based upon the first data ($\epsilon_b$) generated in step 203 and the denominator is based upon the second data ($\epsilon_w$) generated in step 203. The criterion function has the general form:

$$f(\hat{w}) = C\left(\frac{\hat{w}^T \varepsilon_b \hat{w}}{\hat{w}^T \varepsilon_w \hat{w}}\right)$$

where $\hat{w}$ is a vector in the direction whose variation is being tested, and C is a constant based upon the degrees of freedom in $\epsilon_b$ and $\epsilon_w$.

For example, the constant C may be determined as follows:

$$C = \frac{1/\text{degrees of freedom in } \varepsilon_b}{1/\text{degrees of freedom in } \varepsilon_w} = \frac{1/(N-1)}{1/(\Sigma n_i - N)}$$

where N represents the number of groups of items, $n_i$ represents the number of items in a group, and $\Sigma n_i$ represents the sum of $n_i$ for the N groups, and The set of component vectors is determined by solving for those $\hat{w}$ that maximize the criterion function $f(\hat{w})$. An example of the operation of the computer processing system 100 in determining the set of component vectors is set forth below with respect to FIG. 3. For the sake of description, the number of component vectors belonging to this set is denoted D.

Figure 3:
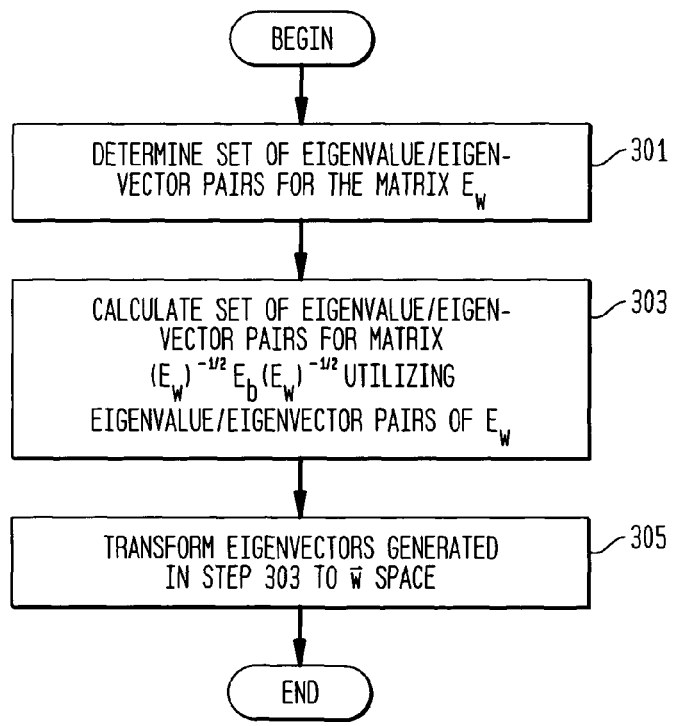
FIG. 3 is a flow chart illustrating operations of step 205 in FIG. 2 in generating a set of component vectors that maximize an F distributed criterion function in accordance with the present invention.

In step 207, a loop is performed over the set of component vectors generated in step 205 (i.e., k=1 . . . D) to calculate the value, denoted $f_k$, of the criterion function $f(\hat{w})$ at the given component vector $\hat{w}$. If the operation set forth below with respect to FIG. 3 is used, the loop of step 207 may be performed over the set of vectors $\vec{\gamma}$, and the value $f_k$ for a given vector $\vec{\gamma}$ may be calculated as follows:

$$f(\hat{\gamma}) = \vec{\gamma}^T (\epsilon_w)^{-1/2} \epsilon_b (\epsilon_w)^{-1/2} \hat{\gamma}$$

where $$\vec{\gamma} = (\epsilon_w)^{1/2} \hat{w}, \text{ and}$$

where $\hat{\gamma}$ is the unit vector corresponding to the vector $\vec{\gamma}$.

In addition, in step 207, the value $f_k$ of the criterion function $f(\hat{w})$ at the given component vector $\hat{w}$ and the associated component vector $\hat{w}$ (or the value $f_k$ of the criterion function $f(\hat{\gamma})$ at the given vector $\hat{\gamma}$ and associated vector $\hat{\gamma}$) are stored by the processing system 100.

In step 209, an F distributed statistic is generated for subsets of the set of component vectors generated in step 205. The F distributed statistic for a given subset of component vectors preferably represents a ratio of the variance between groups of items to the variance within groups of items along the given subset of component vectors. In this case, the statistic, denoted $\psi_s$, characterizing a given subset of component vectors preferably has following form:

$$\psi_s = C\left(\frac{1}{L_S}\right) \Sigma f_k$$

where $f_k$ represents the value of the criterion function $f(\vec{w})$ at a given component vector in the subset, C is a constant, $L_S$ represents the number of $f_k$ values in the given subset of component vectors, and the $\Sigma$ operation sums over the $L_S$ $f_k$ values in the given subset of component vectors.

Note that in the example above where $$C = \frac{1/(N-1)}{1/(\Sigma n_i - N)},$$

the $\psi_s$'s are F distributed with the $((N-1)L_S)$ degrees of freedom in the numerator and $(\Sigma n_i - N)$ degrees of freedom in the denominator.

An optimal subset S of the component vectors is then selected by identifying a subset of component vectors such that a probability value for the statistic $\psi_s$ associated with the subset (preferably, the probability value represents that the probability that the statistic $\psi_s$ for the subset could have been larger by chance) satisfies a predetermined criterion (significance level). This significance level represents a threshold at which an hypothesis that the aggregate F-distributed ratios (for the subset) representing discrimination between groups of items is smaller than that within groups of items can be rejected. A small significance level implies a very significant rejection of this hypothesis, in turn implying high confidence in the hypothesis that the aggregate F-distributed ratios (for the subset) representing discrimination between groups of items is greater than or equal to that within groups of items. In this case, the optical subset S of the component vectors is selected by identifying the subset of component vectors whose probability value for the statistic $\psi_s$ associated with the subset is a minimum. This minimum probability value implies a maximum confidence in the hypothesis that the aggregate F-distributed ratios (for the subset) representing discrimination between groups of items is greater than or equal to that within groups of items. Selection of the optimal subset S is preferably accomplished as follows.

In step 211, the D $f_k$ values generated in step 207 are ranked in descending order (i.e., from largest to smallest).

In step 213, a loop is performed over subsets of component vectors whereby, for each subset, the statistic $\psi_s$ associated with the subset is generated and a probability value for statistic $\psi_s$ is calculated. Preferably, the loop is performed over a counter X ranging from 1 to D. In each iteration of the loop, the following operations are performed. First, the largest X $f_k$ values identified in step 211 are added together as follows $$\left(F_X = \psi_s = C * \left(\frac{1}{L_S}\right) * (f_{k_1} + f_{k_2} + \ldots f_{k_X})\right),$$

and the resultant sum is normalized by a division by X (i.e., $F_X = F_X/X$). Second, a probability value, denoted $p_x$, for the normalized sum $F_X$ is calculated. Third, the probability value $p_x$ and associated counter X are stored.

The probability value $p_x$ for a normalized sum $F_X$ may be calculated in step 213 as follows:

$$p_x = Q(F_x|N-1, X)$$

A more detailed description of the calculation of the probability value $p_x$ for a subset of component vectors may be found in Press et al., "Numerical Recipes", Cambridge University Press, 1986, pp. 175-190, herein incorporated by reference in its entirety. And a more detailed description of the F distribution function is set forth in Freund, "Mathematical Statistics", 5th Ed., Prentice Hall, 1992, pp. 314-315, herein incorporated by reference in its entirety.

In step 215, one or more probability values $p_x$ generated in step 213 that satisfy a predetermined criterion are selected, and the corresponding subset of component vectors corresponding to selected probability value(s) is identified as the optimal subset S of component vectors. Preferably, in step 215, the minimum probability value $p_x$ generated in step 213 is selected, and the corresponding subset of component vectors corresponding to selected probability value is identified as the optimal subset S of component vectors.

Finally, in step 217, one or more of the descriptor vectors for the series of items are mapped to a space corresponding to the optimal subset S of component vectors. This mapping is preferably accomplished for a given descriptor vector $\vec{x}_{ij}$ by performing a loop over each component vector $\vec{w}$ belonging to the optimal subset S of component vectors whereby, in each iteration of the loop, the contribution $\hat{w}^T\vec{x}_{ij}$ (where $\hat{w}^T$ is the transpose of the unit vector $\hat{w}$ for the given component vector $\vec{w}$) is added to a running sum. Consider an example wherein the optimal subset S includes three component vectors ($\vec{w}_1, \vec{w}_2, \vec{w}_3$). In this example, the mapping, denoted M, may be represented by the following:

$$M(\vec{x}_{ij}) = (\hat{w}_1\vec{x}_{ij})\hat{w}_1 + (\hat{w}_2\vec{x}_{ij})\hat{w}_2 + (\hat{w}_3\vec{x}_{ij})\hat{w}_3$$

(where $\hat{w}_1$ is the transpose of the unit vector $\hat{w}_1$ for the component vector $\vec{w}_1$, where $\hat{w}_2$ is the transpose of the unit vector $\hat{w}_2$ for the component vector $\vec{w}_2$, where $\hat{w}_3$ is the transpose of the unit vector $\hat{w}_3$ for the component vector $\vec{w}_3$).

FIG. 3 illustrates an example of the operation of the computer processing system 100 in determining the set of component vectors (i.e., those $\hat{w}$) that maximize the criterion function $f(\hat{w})$. The approach defines a vector $\vec{\gamma}$ that is a function of $\hat{w}$ along which the contribution from the denominator of the criterion function $f(\hat{w})$ is independent.

In step 301, the set of eigenvalue/eigenvector pairs of the matrix $\epsilon_w$ are calculated. This may be accomplished, for example, with the techniques set forth in Press et al., "Numerical Recipes", Cambridge University Press, 1986, pp. 349-363, herein incorporated by reference in its entirety. The set of eigenvalue/eigenvector pairs for which the eigenvalue is non-zero, denoted set $E_w$, is then stored by the computer processing system 100. For the sake of description, the number of eigenvalue/eigenvector pairs belonging to set $E_w$ is denoted K, and a given eigenvalue/eigenvector pair belonging to set $E_w$ is denoted ($e_k, \vec{v}_k$).

The operations may then define a vector, denoted $\vec{\gamma}$, as a function of $\vec{w}$ as follows:

$$\vec{\gamma} = (\epsilon_w)^{1/2}\vec{w}$$

where $$(\epsilon_w)^{1/2} = \Sigma \hat{v}_k \hat{v}_k^T (e_k)^{1/2}$$

where $\hat{v}_k$ is the unit vector corresponding to eigenvector $\vec{v}_k$ and the $\Sigma$ operation sums over the K eigenvalue/eigenvector pair belonging to set $E_w$.

The criterion function $f(\hat{w})$ may be rewritten as $f(\hat{\gamma})$ as follows:

$$f(\hat{\gamma}) = \hat{\gamma}^T (\epsilon_w)^{-1/2} \epsilon_b (\epsilon_w)^{-1/2} \hat{\gamma}$$

where $\hat{\gamma}$ is the unit vector corresponding to the vector $\vec{\gamma}$.

The set of vectors $\vec{\gamma}$ that maximize the criterion function $f(\vec{\gamma})$ may be generated by solving the following eigenvalue equation:

$$(\epsilon_w)^{-1/2} \epsilon_b (\epsilon_w)^{-1/2} \hat{v}_{\bar{k}} = f_{\bar{k}} \hat{v}_{\bar{k}}$$

Finally, the set of vectors $\hat{\gamma}$ that maximize the criterion function $f(\hat{\gamma})$ may then be transformed to generate the corresponding set of component vectors $\hat{w}$ that maximize the criterion function $f(\hat{w})$ as follows:

$$\hat{w} = (\epsilon_w)^{-1/2} \hat{\gamma}$$

In step 303, the computer processing system 100 calculates the matrix $(\epsilon_w)^{-1/2} \epsilon_b (\epsilon_w)^{-1/2}$ utilizing the eigenvalue/ eigenvector pairs belonging to set $E_w$ calculated in step 301. Note that $(\epsilon_w)^{1/2}$ may be calculated as follows:

$$(\epsilon_w)^{1/2} = \Sigma \hat{v}_{\bar{k}} \hat{v}_{\bar{k}}^T (e_k)^{1/2}$$

where $\hat{v}_{\bar{k}}$ is the unit vector corresponding to eigenvector $\vec{v}_{\bar{k}}$ and the $\Sigma$ operation sums over the K eigenvalue/eigenvector pair belonging to set $E_w$.

In addition, in step 303, the computer processing system 100 calculates the set of eigenvalue/eigenvector pairs for the matrix $(\epsilon_w)^{-1/2} \epsilon_b (\epsilon_w)^{-1/2}$. This may be accomplished, for example, with the techniques set forth in Press et al., "Numerical Recipes", Cambridge University Press, 1986, pp. 349-363, incorporated by reference above in its entirety. The set of eigenvalue/eigenvector pairs for which the eigenvalue is non-zero, denoted set $E_{wb}$, is then stored by the computer processing system 100. For the sake of description, the number of eigenvalue/eigenvector pairs belonging to set $E_{wb}$ is denoted K', and a given eigenvalue/eigenvector pair belonging to set $E_{wb}$ is denoted $(e_{k'}, \vec{v}_{k'})$. The K' eigenvectors (each denoted $\vec{v}_{k'}$) of the eigenvalue/eigenvector pairs belonging to set $E_{wb}$ represent the set of vectors $\vec{\gamma}$ that maximize the criterion function $f(\vec{\gamma})$.

In step 305, the computer processing system 100 transforms the K' eigenvectors (each denoted $\vec{v}_{k'}$) of the eigenvalue/eigenvector pairs belonging to set $E_{wb}$ to a set of corresponding component vectors in $\vec{w}$ space (each denoted $\vec{w}_k$) as follows:

$$\vec{w}_k = (\epsilon_w)^{-1/2} \vec{v}_{k'}$$

The K' set of vectors (each denoted $\vec{w}_k$) represent the set of component vectors that maximize the criterion function $f(\vec{w})$.

As described above, the computer implemented method of the present invention provides a mapping (i.e., a transformation) for the descriptor vectors for a series of items to a space that optimally discriminates between groups of items. The method may be used in many domains.

For example, in the domain of bio-informatics, the items of interest may be genotypes that are partitioned into groups based upon phenotypes exhibited by such genotypes; and the descriptor vectors associated with such genotypes may represent biological, chemical, and/or physical properties of such genotypes. Typically, a candidate genotype and associated descriptor vector is identified and one wished to ascertain to which group the candidate genotype belongs. The method discussed above may be used to provide a suggestion as to which group the candidate genotype belongs.

More specifically, the method described above is used to map the descriptor vector for each genotype to a space that optimal discriminates between groups. In addition, the statistical mean of the mapped descriptor vectors for each group [or some other statistical variable (such as the covariance about the mean) based upon the mapped descriptor vectors] is calculated. In addition, the mapping function that optimally discriminates between groups is applied to the descriptor vector for the candidate genotype. A suggestion as to which group the candidate genotype belongs is then determined based upon differences between the mapped descriptor vector for the candidate genotype and the statistical mean of the mapped descriptor vectors for the groups.

In order to illustrate this example in more detail, consider the case where the genotypes are a population of male patients partitioned into two groups (A,B) based upon prostate cancer activity experienced by the patients (i.e., patients belonging to group A have not experienced any prostate cancer activity, and patients belonging to group B have experienced prostate cancer activity). In addition, the descriptor vector associated with each male patient is expression data acquired from a gene probe array system, such as the GeneChipsystems developed by Affymetrix, Inc. In addition, a candidate and associated descriptor vector has been identified. Again, the descriptor vector associated with the candidate is expression data acquired from a gene probe array system, and one wishes to ascertain to which group the candidate belongs. The method discussed above may be used to provide a suggestion as to which group the candidate belongs. More specifically, the method described above is used to map the descriptor vector for each patient to a space that optimally discriminates between groups. In addition, the statistical mean of the mapped descriptor vectors for each group (or some other statistical variable, such as the covariance about the mean, based upon the mapped descriptor vectors) is calculated. In addition, the same mapping function is applied to the descriptor vector for the candidate. Finally, a suggestion as to which group the candidate belongs is determined based upon differences between the mapped descriptor vector for the candidate and the statistical mean of the mapped descriptor vectors for the groups A,B.

In another example in the domain of bio-informatics, the items of interest may be gene sequences that are partitioned into groups; and the descriptor vectors associated with such gene sequences may represent expression activities of such gene sequences. The method discussed above may be used to derive a probability value for the statistic $\psi_s$ that represents a significance level at which an hypothesis that the aggregate F-distributed ratios representing discrimination between groups of expression activities of gene sequences is smaller than that within groups of expression activities of gene sequences can be rejected. A small significance level implies a very significant rejection of this hypothesis, in turn implying high confidence in the hypothesis that the aggregate F-distributed ratios representing discrimination between groups of expression activities of gene sequences is greater than or equal to that within groups of expression activities of gene sequences. In the event that this probability value is less than a threshold value, there is a suggestion that the gene sequences express differences in activities.

In the domain of computational biology and chemistry, for example, the items of interest may be molecular complexes (a molecule or portion of a molecule) that are partitioned into groups based upon a biological activity (for example, molecular complexes belonging to a group all bind to anther molecular complex); and the descriptor vectors associated with such molecular complexes may represent the physical property (structure, charge distribution), biological property and/or chemical property of such molecular complexes. For instance, the descriptor vectors associated with a molecule may be based upon data representing the structure and/or charge distribution of molecule as outlined in i) U.S. Pat. No. 5,784,294 to Platt et al., which is commonly assigned to the assignee of the present invention, ii) R. D. Cramer et al., "Comparative Molecular Field Analysis (CoMFA). Effect of Shape on Binding of Steroids to Carrier Proteins, J. Am. Chem. Soc. Vol. 110, 1988 pp. 5959-5867, iii) A. C. Good et al., "Structure-Activity Relationships from Molecular Similarity Matrices," J. Med. Chem., Vol. 36, 1993, pp. 433-438, iv) A. Jain et al., "Predicting Biological Activities from Molecular Surface Properties. Performance Comparisons on a Steroid Benchmark," J. Med. Chem., Vol. 37, 1994, pp. 2315-2327, v) W. Fisanick et al., "Similarity Searching on CAS Registry Substances, 1: Global Molecular Property and Generic Atom Triangle Geometric Searching," Journal of Chemical Information and Computer Sciences, Vol. 32, No. 6, 1992, pp. 664-674, and W. Fisanick et al., "Similarity Searching on CAS Registry Substances, 2: 2D Structural similarity," Journal of Chemical Information and Computer Sciences, Vol. 34, No. 1, 1994, pp. 130-140, hereinafter incorporated by reference in their entirety. Similarly, descriptor vectors may be associated with a portion of a molecule (i.e., a subset of the atoms that make up a molecule) and represent the structure and/or change distribution of the portion of the molecule. In such domains, typically, a candidate molecular complex and associated descriptor vector is identified and one wishes to ascertain to which group the candidate molecular complex belongs. The computer implemented method of the present invention described above may be used to provide a suggestion as to which group the candidate molecular complex belongs. More specifically, the method described above is used to map the descriptor vector for each molecular complex to a space that optimal discriminates between groups. In addition, the statistical mean of the mapped descriptor vectors for each group [or some other statistical variable (such as the covariance about the mean) based upon the mapped descriptor vectors] is calculated. In addition, the mapping function that optimally discriminates between groups is applied to the descriptor vector for the candidate molecular complex. A suggestion as to which group the candidate molecular complex belongs is then determined based upon differences between the mapped descriptor vector for the candidate molecular complex and the statistical mean of the mapped descriptor vectors for the groups.

Figure 4:
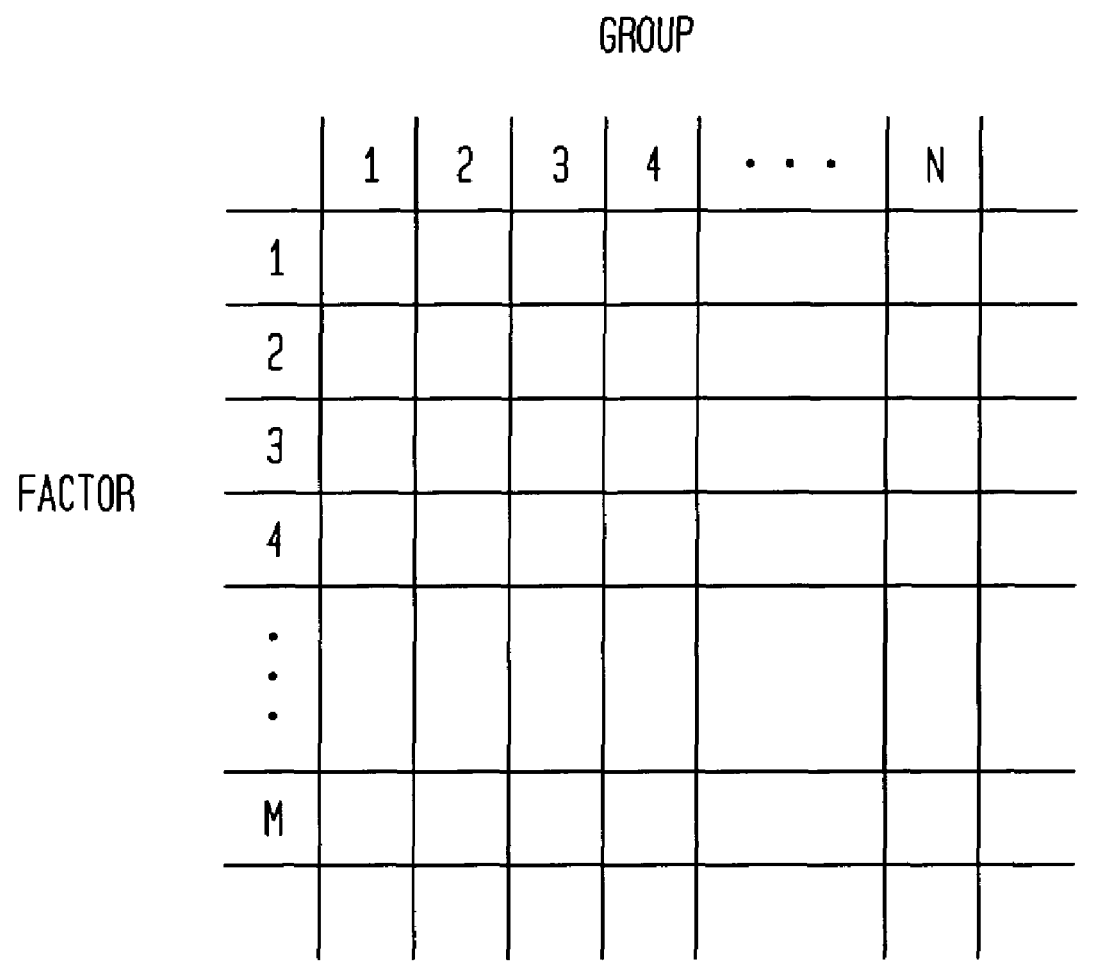

The description above illustrates application of the present invention in one-way analysis of variance. However, the present invention is not limited in this respect, and can be applied to multi-factor designs with multi-way analysis of variance. An example of such a design for an item of interest is illustrated in FIG. 4. In this design, a series of items are classified into N groups (N is an integer greater than 1), wherein each group is identified by an identifier i ranging from 1 to N represented by the columns of the matrix. A series of factors (typically each factor represents one or more experimental treatments) are attributed to the items belonging to the groups, wherein each factor is identified by an identifier j ranging from 1 to M represented by the rows of the matrix. An identifier $m_{ijk}$ identifies item k that is attributed to the group/factor pair i,j, and vector $\vec{x_{ijk}}$ identified a descriptor vector attributed to the item $m_{ijk}$. Preferably, the descriptor vectors are stored as part of a file in persistent storage and loaded into non-persistent storage for use by the CPU 103 as needed.

In such a system, one may break any given descriptor vector $\vec{x_{ijk}}$ into the following components:

$$\vec{x_{ijk}} = \vec{a} + \vec{\beta_i} + \vec{\gamma_j} + \vec{\delta_{ij}} + \vec{\epsilon_{ijk}},$$

where $\vec{a}$ represents the mean of the descriptor vectors for all the items (of all the groups and all the factors);

$\vec{\beta_i}$ represents the mean of the descriptor vectors for all the items in group i (of all the factors);

$\vec{\gamma_j}$ represents the mean of the descriptor vectors for all the items in factor j (of all the groups);

$\vec{\delta_{ij}}$ represents the mean of the deviation of the descriptor vectors for all the items in group/factor pair i,j from the sum ($\vec{a} + \vec{\beta_i} + \vec{\gamma_j}$); and $\vec{\epsilon_{ijk}}$ represents deviation from the mean $\vec{\delta_{ij}}$ to the descriptor vector $\vec{x_{ijk}}$.

These values may be calculated as follows. For each group/factor pair i,j of items (i.e., i ranging from 1 to N, and j ranging from 1 to M), the mean of the descriptor vectors within group/factor pair i,j, denoted $\vec{x_{ij.}}$, may be calculated as follows:

$$\vec{x_{ij.}} = \frac{1}{n_{ij}} \sum \vec{x_{ijk}}$$

where $n_{ij}$ represents the number of items in the group/factor pair i,j, and the $\Sigma$ operator sums over the range (k=1 . . . $n_{ij}$) of items in the group/factor pair i,j Then, for each group i of items (i.e., i ranging from 1 to N), the mean $\vec{x_{i..}}$ may be calculated as follows:

$$\vec{x_{i..}} = \frac{1}{n_i} \sum \vec{x_{ij.}}$$

where $n_i$ represents the number of items in the group i, and the $\Sigma$ operator sums over the range (1 . . . M) of factors Then, for each factor j (i.e., i ranging from 1 to M), the mean $\vec{x_{.j.}}$ may be calculated as follows:

$$\vec{x_{.j.}} = \frac{1}{n_j} \sum \vec{x_{ij.}}$$

where $n_j$ represents the number of items in the factor j, and the $\Sigma$ operator sums over the range (1 . . . N) of groups Then, the mean $\vec{a}$ may be calculated as follows:

$$\vec{a} = \frac{1}{N} \sum \vec{x_{i..}}$$

where N represents the number of groups, and the $\Sigma$ operator sums over the range (1 . . . N) of groups; or equivalently $$\vec{a} = \frac{1}{M} \sum \vec{x_{.j.}}$$

where M represents the number of factors, and the $\Sigma$ operator sums over the range (1 . . . M) of factors For each group i of items (i.e., i ranging from 1 to N), the mean $\vec{\beta_i}$ may be calculated as follows:

$$\vec{\beta_i} = \vec{x_{i..}} - \vec{a}$$

For each factor j of items (i.e., j ranging from 1 to M), the means $\vec{\gamma}_j$ may be calculated as follows:

$$\vec{\gamma}_j = \overline{\vec{x}_{j.}} - \vec{a}$$

For each group/factor pair i,j of items (i.e., i ranging from 1 to N, and j ranging from 1 to M), the means $\vec{\delta}_{ij}$ may be calculated as follows:

$$\vec{\delta}_{ij} = \overline{\vec{x}_{ij.}} - \overline{\vec{x}_{j.}}$$

Finally, for each descriptor vector $\vec{x}_{ijk}$ in the group/factor pair i,j, the deviation $\vec{\epsilon}_{ijk}$ may be calculated as follows:

$$\vec{\epsilon}_{ijk} = \vec{x}_{ijk} - \vec{\delta}_{ij}$$

The total covariance, denoted $\epsilon$, may be represented by the sum of the following four (4) terms:

(1) $\Sigma M_i \vec{\beta}_i \vec{\beta}_i^T$, where the $\Sigma$ operator sums over the range of groups i=1 to N and $M_i$ is the number of items in group i.

(2) $\Sigma N_j \vec{\gamma}_j \vec{\gamma}_j^T$, where the $\Sigma$ operator sums over the range of factors and Nj is the number of items in factor i.

(3) $\Sigma N_{ij} \vec{\delta}_i \vec{\delta}_i^T$, where the $\Sigma$ operator sums over the range of group/factor pairs i,j and $N_{ij}$ is the number if items belonging to the group/factor pair i,j.

(4) $\Sigma \vec{\epsilon}_{ijk} \vec{\epsilon}_{ijk}^T$, where the $\Sigma$ operator sums over the range of group/factor pairs i,j and k items in each group/factor pair i,j.

Note the first term represents the covariance between groups of items; the second term represents the covariance between factors; and the third term represents the covariance of the interaction between the groups and factors.

Generally, the principles of the present invention as described above may then be used to map the components of the descriptors vectors of the items to a space that:
1) optimally discriminates between the groups of items;
2) optimally discriminates between factors; or
3) optimally discriminates interactions between the groups and factors.

More specifically, in order to map the components of the descriptors vectors of the items to a space that optimally discriminates between groups of items (case 1 above), an F distributed criterion function is used to determine a set of components vectors that maximize the criterion function. The criterion function has a numerator and a denominator, whereby the numerator is based upon the covariance between groups of items (the first term described above) and the denominator is based upon the fourth term described above. The criterion function has the general form:

$$f(\vec{w}) = C \left( \frac{\vec{w}^T \left( \sum M_i \vec{\beta}_i \vec{\beta}_i^T \right) \vec{w}}{\vec{w}^T \left( \sum \vec{\epsilon}_{ijk} \vec{\epsilon}_{ijk}^T \right) \vec{w}} \right)$$

where $\vec{w}$ is some vector

Figure 2B:
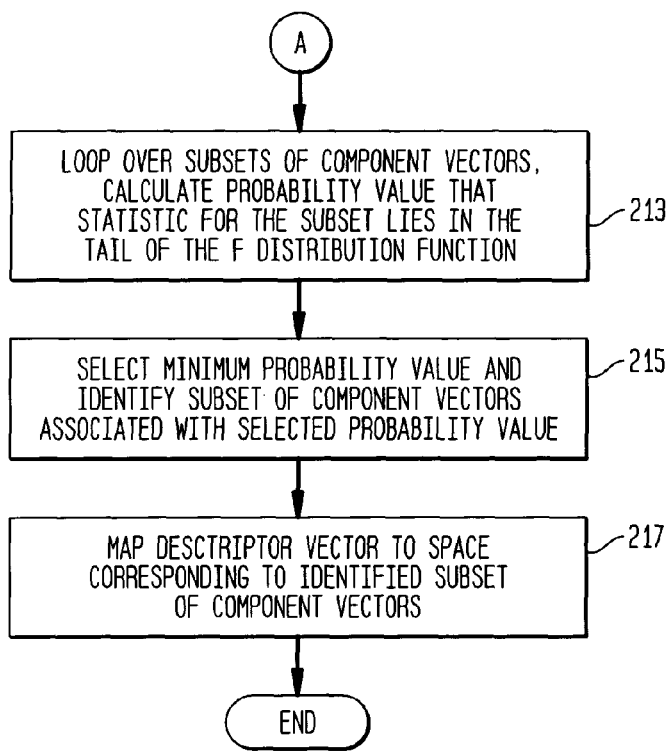

The set of component vectors is determined by solving for those $\vec{w}$ that maximize the criterion function $f(\vec{w})$, and an optimal subset of the component vectors is identified. A more detailed description of this operation is described above with respect to steps 205-215 of FIG. 2. Finally, the components of the descriptor vectors for the items are mapped to a space corresponding to the optimal subset of the component vectors. The resultant data optimally discriminates between groups of items. A more detailed description of this operation is described above with respect to step 217 of FIG. 2.

In order to map the components of the descriptors vectors of the items to a space that optimally discriminates between factors (case 2 above), an F distributed criterion function is used to determine a set of component vectors that maximize the criterion function. The criterion function has a numerator and a denominator, whereby the numerator is based upon the covariance between factors (the second term described above) and the denominator is based upon the fourth term described above. The criterion function has the general form:

$$f(\vec{w}) = C \left( \frac{\vec{w}^T \left( \sum N_j \vec{\gamma}_j \vec{\gamma}_j^T \right) \vec{w}}{\vec{w}^T \left( \sum \vec{\epsilon}_{ijk} \vec{\epsilon}_{ijk}^T \right) \vec{w}} \right)$$

where $\vec{w}$ is some vector

The set of component vectors is determined by solving for those $\vec{w}$ that maximize the criterion function $f(\vec{w})$, and an optimal subset of the component vectors is identified. A more detailed description of this operation is described above with respect to steps 205-215 of FIG. 2. Finally, the components of the descriptor vectors for the items are mapped to a space corresponding to the optimal subset of the component vectors. The resultant data optimally discriminates between factors. A more detailed description of this operation is described above with respect to step 217 of FIG. 2.

In order to map the components of the descriptors vectors of the items to a space that optimally discriminates interactions between the groups and factors (case 3 above), an F distributed criterion function is used to determine a set of component vectors that maximize the criterion function. The criterion function has a numerator and a denominator, whereby the numerator is based upon the covariance of the interaction between the groups and factors (the third term described above) and the denominator is based upon the fourth term described above. The criterion function has the general form:

$$f(\vec{w}) = C \left( \frac{\vec{w}^T \left( \sum N_{ij} \vec{\delta}_i \vec{\delta}_i^T \right) \vec{w}}{\vec{w}^T \left( \sum \vec{\epsilon}_{ijk} \vec{\epsilon}_{ijk}^T \right) \vec{w}} \right)$$

where $\vec{w}$ is some vector

The set of component vectors is determined by solving for those $\vec{w}$ that maximize the criterion function $f(\vec{w})$, and an optimal subset of the component vectors is identified. A more detailed description of this operation is described above with respect to steps 205-215 of FIG. 2. Finally, the components of the descriptor vectors for the items are mapped to a space corresponding to the optimal subset of the component vectors. The resultant data optimally discriminates interaction between the groups and factors. A more detailed description of this operation is described above with respect to step 217 of FIG. 2.

The application of the present invention to multi-factor designs may be used in many domains.

In the domain of insurance, for example, the items of interest may be individuals that are partitioned into groups based upon certain characteristics such as age, gender, etc. Categories of auto insurance polices (for example, categorized based upon the limits/deductible amount for liability coverage and/or collision coverage) attributed to the groups of individual may represent the factors of the design. The descriptor vectors associated with such individuals may represent risk of the individual (for example, may be a dollar amount of the moneys paid to the individual arising from auto insurance claims during a predetermined period of time). In this example, the computer implemented method discussed above may be used to provide a mapping of the components of the descriptor vectors to a space that optimal discriminates between groups of individuals; or optimally discriminates between the policies, or optimally discriminates interaction between the groups and policies.

In the domain of agriculture, for example, the items of interest may be plant species that are partitioned into groups based upon certain characteristics such as genetic makeup of the plant species. Categories of fertilizers (or pesticides) that are applied to the groups of plant species may represent the factors of the design. The descriptor vectors associated with such plant species may represent a characteristic of the plant species such as yield and/or drought resistance. In this example, the computer implemented method discussed above may be used to provide a mapping of the components of the descriptor vectors to a space that optimal discriminates between groups of plant species; or optimally discriminates between the fertilizers (or pesticides), or optimally discriminates interaction between the groups and fertilizers (or pesticides).

It should be noted that the information encoded by the descriptor vectors may cause membership in a group associated with an item of interest. For example, the behavior of a molecular complex, which is encoded by a descriptor vector associated with the molecular complex, may cause membership in a group (or category) of molecular complexes (for example, hydrophilic, polar, "active" with respect to a class of reactions, etc.). In the alternative, the information encoded by the descriptor vector associated with an item of interest may be a response to group membership. For example, the risks associated with an insurance policy may be encoded by a descriptor vector associated with the insurance policy, whereby the risks are dictated by the group (i.e., type) membership of the policy.

In addition, the present invention may be used to identify molecules within a large database of molecules that are similar to a query molecule. The methodology may be conceptually divided into three phases: a training phase, an acquisition phase, and a recognition phase.

Figure 5:
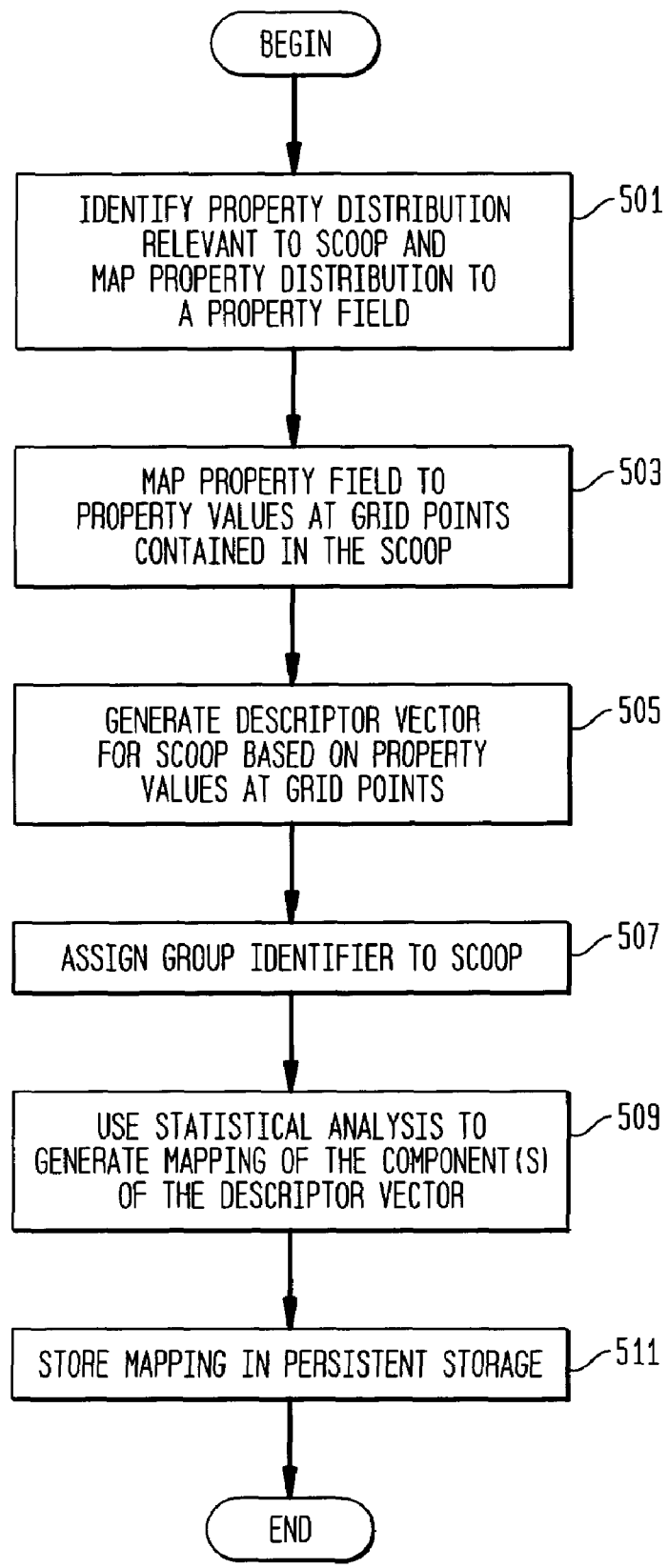
FIG. 5 is a flow chart illustrating the training phase of a system that identifies molecules within a database of molecules that has similar structure to a query molecule in accordance with the present invention.

In the training phase, for each molecules in a series of molecules (denoted the training set), the following steps are performed for a given molecule in the training set. Data that represents the atomic structure of the given molecule in the training set is stored in persistent memory. In addition, data that represents one or more properties of the given molecule is stored in persistent memory. The data that represents the atomic structure of the given molecule is read from persistent memory and used to define a set of three-dimensional regions of space that contain portions of the given molecule. For each region of the given molecule, one or more properties of the given molecule are generated and mapped to a one or more property values for the grid points of the region; and the properties values for the grid points of the region are used to determine a descriptor vector associated with the region that characterizes the region. Preferably, one or more components of the descriptor vector associated with a given region represent position and/or orientation of axes derived from the property distribution of the region, wherein the axes are invariant with respect to translation and rotation of the region. In addition, a group identifier is assigned to the region. The group identifier identifies the group of which the region belongs. For example, the regions may be partitioned into groups based upon the charge distribution of the region (e.g., charged, neutral, polar, non-polar, etc.) or other property or behavior of the region. A mapping of one or more components of the descriptor vector for the regions is then calculated (preferably by applying the method discussed above is used to generate a mapping of components of the descriptor vectors to a space that optimally discriminates between the groups of regions—step 217 of FIG. 2). The mapping generated in the training phase is stored in persistent storage and used in the acquisition phase and recognition phase. A more detailed description of the training phase for a particular region is illustrated in FIG. 5.

Figure 6:
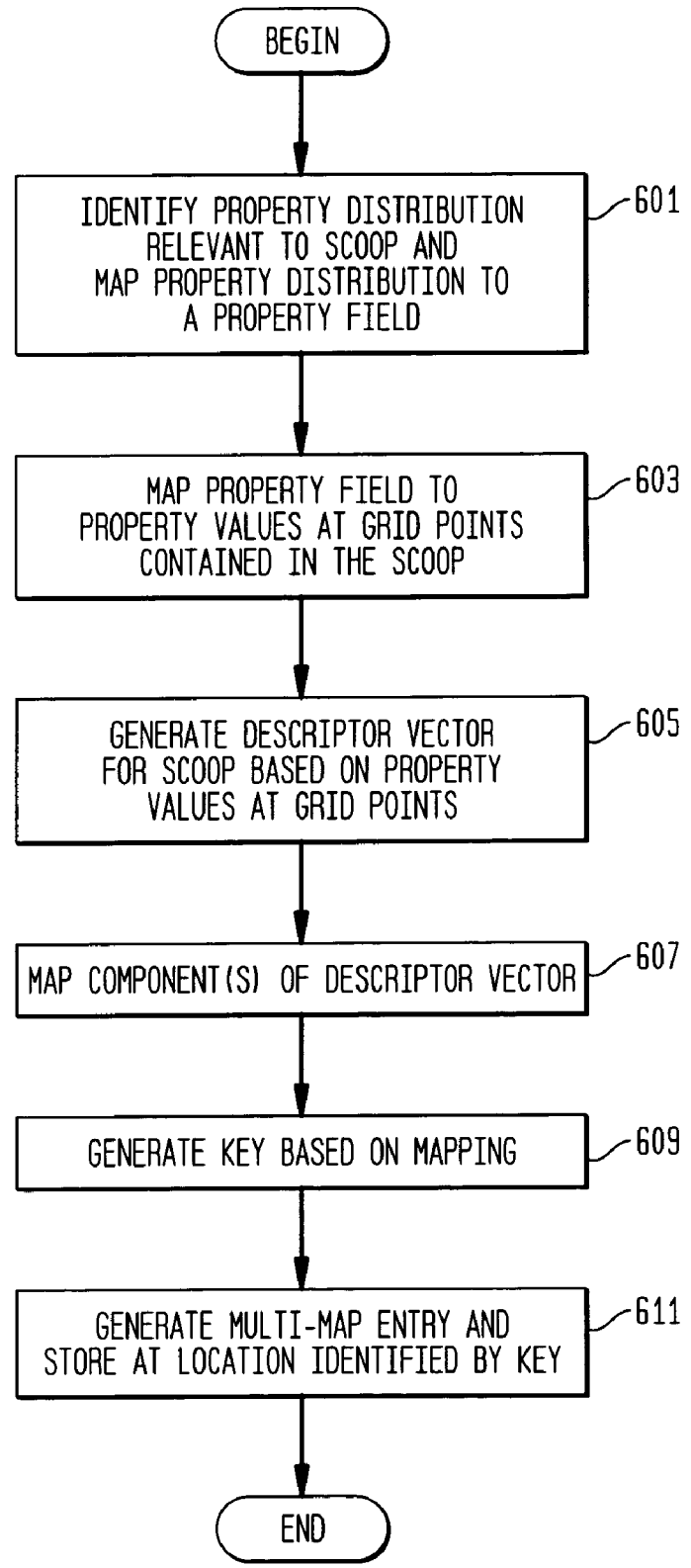
FIG. 6 is a flow chart illustrating the acquisition phase of the present invention, wherein data representing the structure of a given molecule is stored in persistent memory.

In the acquisition phase, for each molecule in a series of molecules (which is typically distinct from the serious of molecules processed in the training phase), the following steps are performed for a given molecule. Similar to the training phase, data that represents the atomic structure of the given molecule is used to define a set of regions that contain portions of the given molecule, and descriptor vectors are generated for such regions of the given molecule. Similar to the training phase, one or more items of the descriptor vector associated with a given region preferably represents position and/or orientation of axes derived from the property distribution of the region, wherein the axes are invariant with respect to translation and rotation of the region. The mapping generated in the training phase is used to map one or more components of the descriptor vector for each given region (preferably to a space that optimally discriminates between groups of regions), and a key is generated based upon the mapping of the component(s) of the associated descriptor vector. The key identifies an entry in a multi-map (described below) stored in persistent memory. Data identifying the given region, data (or a pointer to such data) characterizing a set of axes derived from the property distribution of the region, and preferably other data (for example, data identifying the molecule to which the region belongs, and data representing the geometric center of the molecule to which the region belongs) are then stored in the multi-map at a location identified by the key. As described below in more detail, the data characterizing a set of axes derived from the property distribution of a given region preferably characterizes transformation between an input reference frame and the inertial reference frame for the given region. A more detailed description of an exemplary embodiment of the acquisition phase for a particular region is illustrated in FIG. 6. Note that if there are common molecules (or regions) in the series of molecules processed in the training phase and acquisition phase, data generated in the training phase may be used in the acquisition phase, and the operations that use and/or generate such data may be bypassed accordingly.

Figure 7A:
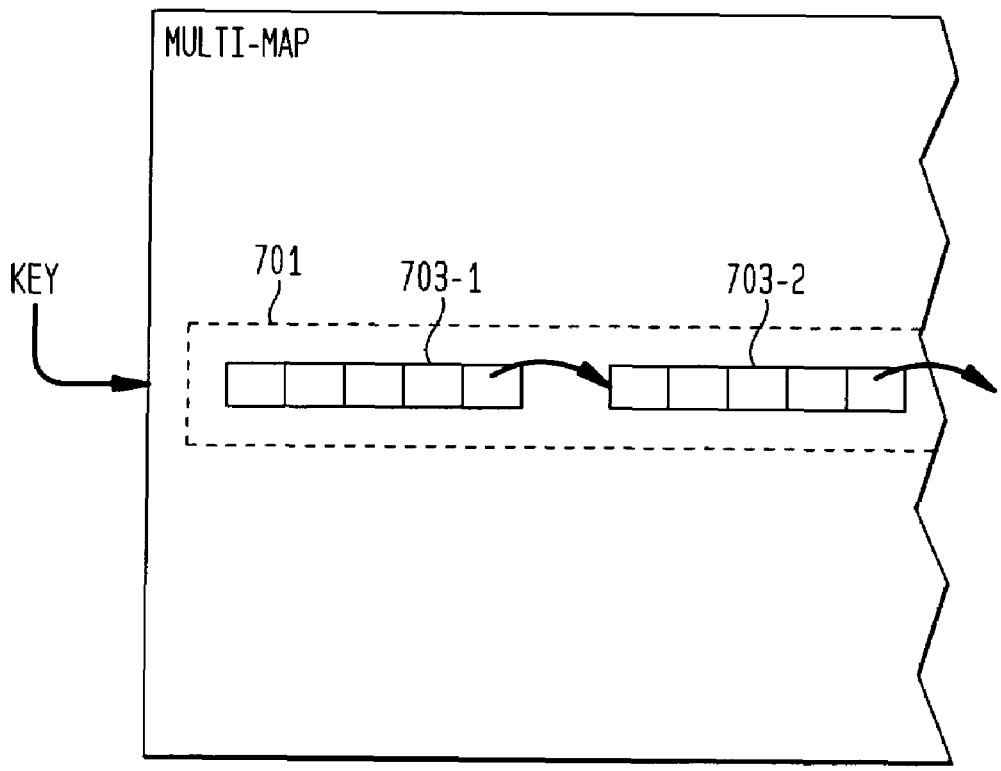
FIGS. 7(A) and (B) is a pictorial illustration of a multimap, which is part of the system that identifies molecules within a database of molecules that has similar structure to a query molecule.

In the recognition phase, a query molecule is provided. Similar to the training and acquisition phase, data that represents the atomic structure of the query molecule is used to define a set of regions that contain portions of the query molecule, and descriptor vectors are generated for such regions of the query molecule. Similar to the training phase, one or more items of the descriptor vector associated with a given region preferably represents position and/or orientation of axes derived from the property distribution of the region, wherein the axes are invariant with respect to translation and rotation of the region. For each query region, the mapping generated in the training phase is used to map one or components of the descriptor vector for the given query region (preferably to a space that optimally discriminates between groups of regions), and a key is generated based upon the mapping of the components(s) of the associated descriptor vector. For each key, a multi-map entry identified by the key is retrieved and data stored therein [i.e., data identifying one or more regions associated therewith, data characterizing a set of axes derived from the property distribution of each region associated therewith, data identifying the molecule to which each region associated therewith belongs, and data representing the geometric center of the molecule to which each region associated therewith belongs] are read from the table. For each region identified by the retrieved table entry, an hypothesized match is constructed and added to a vote table. After processing all of the regions identified by the retrieved table entry, the vote table is sorted to determine a set of potential matching regions, and the set of potential matching regions (and/or the molecules to which the set of potential matching regions belong) is made accessible to the user via an I/O device. A more detailed description of an exemplary embodiment of the recognition phase for a region of the query molecule is illustrated in FIGS. 7(A) and (B).

Training Phase

In the training phase, for each molecule in a training set, data that represents the structure of the given molecule is stored in persistent memory. Preferably, the data represents the atomic structure of the given molecule in an arbitrary three-dimensional reference frame, which is referred to below as the "input reference frame". The data may be obtained from a database (public or private) or be derived by traditional molecular modeling techniques.

In addition, for each molecule in the training set, data that represents the property distribution of one or more properties of the given molecule is generated, for example by reading such data from persistent memory. The property distribution for the property of a given molecule may be an atomic property distribution (i.e., data representing a heuristic, such as electronegativity, hydrophobicity or polarity, that characterizes the behavior or property of an atom in the given molecule), a surface property distribution (i.e., data representing a heuristic that characterizes the behavior or property of a surface on or within the molecule), or a volumetric property distribution (i.e., data characterizing the behavior or property of a region of the molecule—for example, electron density).

In addition, for each given molecule in the training set, the structure data is used to generate a set of three-dimensional regions of space, hereinafter referred to "scoops", in the input reference frame. Preferably, each scoop is a spherical region in the input reference frame having a center (i.e., a point in the input reference frame) and a radius. Preferably, the center of each scoop corresponds to one or more heuristics of the given molecule. For example, the heuristic may correspond to the coordinate of i) the nucleus of one or more atoms of the given molecule, ii) the center of one or more bonds between atoms of the given molecule, iii) the end point of an extension to a bond (typically the length of the extension is a factor of bond length) between atoms of the given molecule, iv) a grid points in the given molecule, v) the geometric center of the molecule, vi) ring centers in the given molecule, or vii) lone pairs of electrons in the given molecule. In addition, the radius of each scoop may be set to a predetermined value (for example, 3 angstroms, or 5 angstroms) or may be base upon heuristics of the given molecule. It should be noted that a scoop can be any arbitrary three-dimensional region in the input reference frame.

As illustrated in FIG. 5, the training phase preferably performs a nested loop over the molecules in the training set; wherein, for a given molecule, each scoop in the set of scoops for the given molecule is processed as follows.

In step 501, the property distribution of one or more properties of the given molecule that is relevant to the scoop are identified, and the relevant property distribution is mapped to a property field that represents the value of the property at points in the input reference frame. There are many well-known techniques to map a property distribution (atomic, surface, volumetric) to a property field, the specifics of which is not relevant to the present invention. Examples of such techniques may be found in U.S. Pat. No. 5,025,388 to Cramer, III et al., hereinafter incorporated by reference in its entirety. With regard to atomic properties for the given molecule, preferably the properties of atoms that are contained within the scoop are identified as relevant properties for the scoop in step 501. With regard to surface properties for the given molecule, preferably the properties of surfaces that are contained (partially or fully) within the scoop are identified as relevant properties for the scoop in step 501. With regard to volumetric properties for the given molecule, preferably the properties of volumes that are contained (partially or fully) within the scoop are identified as relevant properties for the scoop in step 501.

In step 503, the property field generated in step 501 is mapped to grid points contained in the scoop to determine contribution of property field at the grid points. Preferably, the grid points are evenly spaced within the given scoop. In addition, the contribution of the property field at a given grid point preferably includes two values: the first value is a positive value, which for the sake of description is referred to below as a mass value; the second value is a real value, which for the sake of description is referred to below as a charge value. There are many possible techniques to calculate the contribution of a property field at a given grid point, the specifics of which is not relevant to the present invention. For example, the following "smearing function" can be used in step 503 to map values of the points of the property field to a first value $\mu_i$ (mass value) at grid point i:

$$\mu_i = \sum_j A_j * e^{\frac{-R_{ij}}{L_0}} * \left(\frac{1}{R_{ij}+B}\right)$$

where $A_j$ represents the value of the property field at a point j in the property field, $R_{ij}$ represents the distance between the point j in the property field and the point i in the scoop;

$L_0$ is a damping factor, which typically ranges between 0.5 and 2.5;

B is an arbitrary constant, which typically is 1; and $\Sigma$ sums over all the points in the property field for the scoop.

Alternate smearing functions may be gaussian forms. In addition, the following equation may be used to map values of the points of the property field to a second value $\chi_i$ (charge value) at grid point i:

$$\chi_i = \mu_i - \bar{\mu}$$

where $\bar{\mu}$ represents the mean first value (mass value) for all the gird point of the scoop In step 505, a descriptor vector for the scoop is generated based upon the property values of the grid points of the scoop. Preferably, the components of the descriptor vector for the scoop includes one or more of the following data values, details of which are set forth below:

| | |
|---|---|
| ID | data value identifying the molecule from which the scoop is derived |
| N | an integer value representing the number of grid points for the scoop |
| M | total mass for the scoop, which is a sum of the first values (i.e., "mass values" or $\mu_i$) for the grid points of the scoop |
| Q | total charge for the scoop, which is the sum of the second values (i.e., "charge values" or $\chi_i$) for the grid points of the scoop |
| $S_x, S_y, S_z$ | components of a vector describing translation between origin of the input reference frame and center of mass in the input reference frame |
| $I_x, I_y, I_z$ | principal values of the moment of inertia tensor of the scoop with respect to the center of mass of the scoop |
| $S_\Theta, S_\Phi, S_\Omega$ | $S_\Phi, S_\Theta$ are polar angles that describe an axis of rotation. $S_\Omega$ represents an angle of rotation about that angle. Together, the angles represent a rotation transformation between principal axes of the moment of inertia tensor and axes of the input reference frame |
| $v_x, v_y, v_z$ | components of a vector describing translation between the center of scoop in the inertial reference frame and center of mass in the inertial reference frame |
| $d_x, d_y, d_z$ | components of a vector describing translation between center of mass in the inertial reference frame and center of dipole in the inertial reference frame |
| $Ci_x, Ci_y, Ci_z$ | components of a vector describing third order moment of mass about a center of expansion in the internal reference frame |
| $Cq_x, Cq_y, Cq_z$ | components of a vector describing third order moment of charge about a center of expansion in the internal reference frame |
| $Q_{xx}, Q_{xy}, Q_{xz}$ $Q_{yy}, Q_{yz}, Q_{zz}$ | components of a tensor characterizing quadrupolar moment about a center of expansion in the internal reference frame |

Note that the components ID, N, M, Q, $I_x$, $I_y$, $I_z$, $v_x$, $v_y$, $v_z$, $d_x$, $d_y$, $d_z$, $Ci_x$, $Ci_y$, $Ci_z$, $Cq_x$, $Cq_y$, $Cq_z$, $Q_{xx}$, $Q_{xy}$, $Q_{xz}$, $Q_{yy}$, $Q_{yz}$, $Q_{zz}$ characterize the property distribution with respect to invariant axes (i.e., axes that are invariant with respect to translation and rotation of the given scoop—for example the sensed inertial axes of the given scoop). Also note that the components $S_x$, $S_y$, $S_z$, $S_\Theta$, $S_\Phi$, $S_\Omega$ are variant with respect to translation and rotation of the scoop, and characterize orientation of the invariant axes with respect to the input reference frame of the scoop. A more detailed description of the calculation of the components of the descriptor vector for a given scoop is set forth below.

In step 507, a group identifier is assigned to the scoop. The group identifier identifies the group to which the region belongs. For example, the scope may be partitioned into groups based upon the charge distribution of the scoop (e.g., charged, neutral, polar, non-polar, etc.) or other property or behavior of the scoops.

In step 509, statistical analysis is used to generate a mapping of one or more components of the descriptor vector for the scoop. Preferably, the computer implemented method of the present invention discussed above is used to generate a mapping of the component of the descriptor vector for the scoop that characterize position and/or orientation of invariant axes derived from the property distribution of the given scoop (i.e., ID, N, M, Q, $I_x$, $I_y$, $I_z$, $v_x$, $v_y$, $v_z$, $d_x$, $d_y$, $d_z$, $Ci_x$, $Ci_y$, $Ci_z$, $Cq_x$, $Cq_y$, $Cq_z$, $Q_{xx}$, $Q_{xy}$, $Q_{xz}$, $Q_{yy}$, $Q_{yz}$, $Q_{zz}$) to a space that optimally discriminates between the groups of scoops (described above with respect to step 217 of FIG. 2). As described above with respect to step 217 of FIG. 2, the mapping is based upon the transpose of unit vectors for the component vectors $\vec{w_1}$, $\vec{w_2}$, $\vec{w_3}$. The mapping generated in step 509 is preferably stored in persistent storage for subsequent use in the acquisition phase and recognition phase.

Acquisition Phase

In the acquisition phase, for each molecule in a series of molecules, data that represents the structure of the given molecule is stored in persistent memory. Preferably, the data represents the atomic structure of the given molecule in an arbitrary three-dimensional reference frame, which is referred to below as the "input reference frame". The data may be obtained from a database (public or private) or be derived by traditional molecular modeling techniques.

In addition, for each molecule in a series of molecules, data that represents the property distribution of one or more properties of the given molecule is generated, for example, by reading such data from persistent memory. The property distribution for a property of the given molecule may be an atomic property distribution, a surface property distribution, or a volumetric property distribution as described above.

In addition, for each given molecule in the series of molecules, the structure data is used to define a set of scoops in the input reference frame. Preferably, each scoop is a spherical region in the input reference frame having a center and radius as described above.

As illustrated in FIG. 6, the acquisition phase preferably performs a nested loop over the series of molecules, wherein, for a given molecule, each scoop in the set of scoops for the given molecule is processed as follows.

In step 601, properties of the given molecule that are relevant to the scoop are identified, and the relevant properties are mapped to a property field that represents the value of the property at points in the input reference frame. This operation is similar to the processing described above with respect to step 501 of the training phase.

In step 603, the property field generated in step 601 is mapped to grid points contained in the scoop to determine contribution of property field that the grid points. Preferably, the contribution of property field at a given grid point includes two values: a positive mass value and a real charge value. This operation is similar to the processing described above with respect to step 503 of the training phase.

In step 605, a descriptor vector of the scoop is generated based upon the property values of the grid points of the scoop generated in step 603. Preferably, the components of the descriptor vector for the scoop includes one or more of the data values as described above with respect to step 505 of the training phase.

In step 607, the mapping generated in step 509 of the training phase is used to map one or more components of the descriptor vector for the scoop (preferably, the component(s) of the descriptor vector is mapped to a space that optimally discriminates between the groups of scoops as described above with respect to step 217 of FIG. 2).

In step 609, a key is generated based upon the mapping of the component(s) of the descriptor vector for the scoop in step 607. The key identifies an entry in a multi-map stored in persistent memory. The multi-map is an associative memory which permits more than one entry stored in the memory to be associated with the same key. A detailed description of a multi-map is set forth in D. R. Musser and Atul Saini, STL Tutorial and Reference Guide: C++ Programming with the Standard Template Library (Addison-Wesley 1996), herein incorporated by reference in its entirety. Preferably, the multi-map is formed from a hash table. A more detailed description of a hash table may be found in R. Sedgewick, Algorithms in C++ (Addison-Wesley 1992), herein incorporated by reference in its entirety. In the alternative, the multi-map container may be formed from a linked list data structure, or a tree structure such a an AVL-tree or B*tree as described in D. R. Musser and Atul Saini, herein incorporated by reference in its entirety. One skilled in the art will realize that there are many possible underlying implementations for the multi-map data structure.

Finally, in step 611, data identifying the given scoop, data (or a pointer to such data) characterizing a set of axes derived from the property distribution of the scoop, and preferably other data (for example, data identifying the molecule to which the scoop belongs, and data representing the geometric center in the input reference frame of the molecule to which the scoop belongs) are then stored in the multi-map at a location identified by the key generated in step 609. Preferably, the data characterizing a set of axes derived from the property distribution of a given scoop characterizes transformation between an input reference frame and the inertial reference frame for the given scoop—the components $S_x$, $S_y$, $S_z$, $S_\theta$, $S_\Phi$, $S_{106}$ of the descriptor vector for the scoop as discussed above with respect to step 605.

An exemplary multi-map entry is illustrated in FIGS. 7(A) and (B). The entry 701 includes a series of segments 703-1 and 703-2 (two shown) coupled via a link-list data structure. Each segment includes an first ID field 711 that stores an identifier for a scoop, a pointer 713 to data (or the data itself) characterizing a set of axes derived from the property distribution of the scoop, a second ID field 715 identifying the molecule to which the scoop belongs, a pointer 717 to data (or the data itself) representing the geometric center of the molecule to which the scoop belongs, and a pointer 719 to the next segment in the table entry.

The operations of step 601-611 are applied for each scoop in a given molecule. At the end of the acquisition phase, the multi-map stores entries each corresponding to one or more scoops for the series of molecules being studied.

Recognition Phase

Figure 8A:
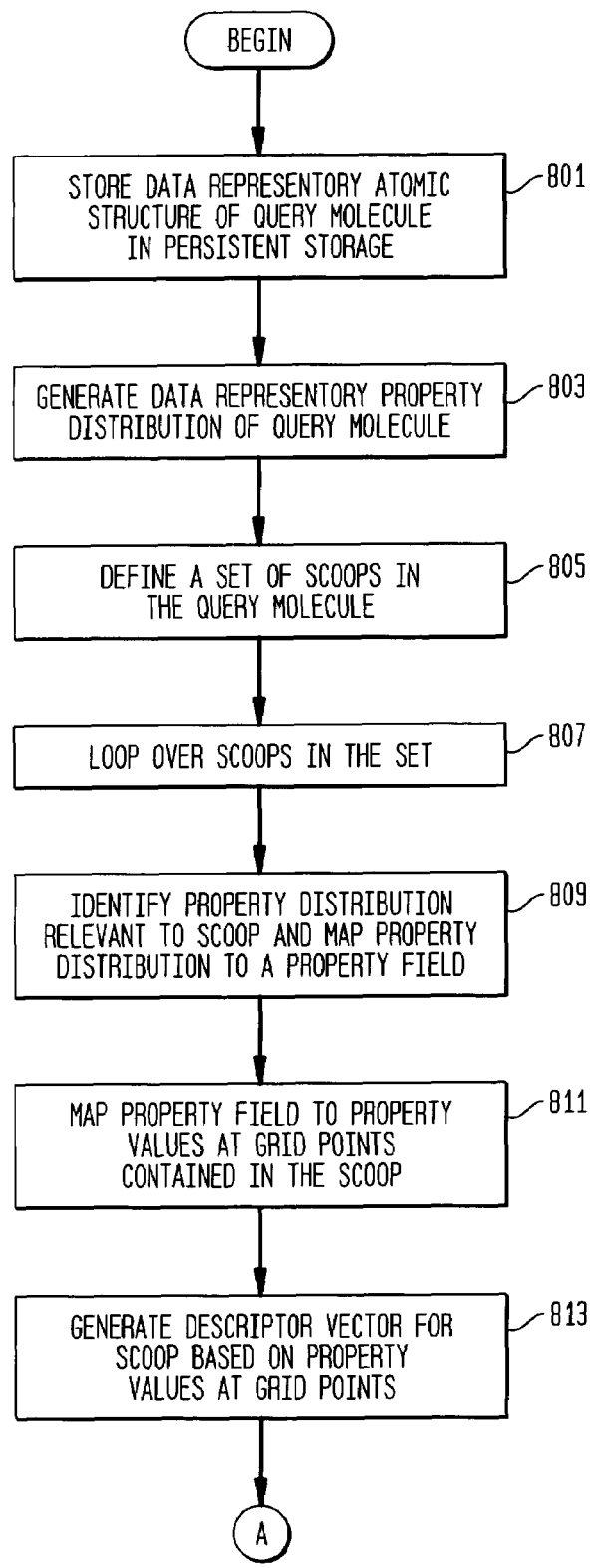
FIGS. 8(A) and (B) is a flow chart illustrating the recognition phase of a system identifies molecules within a database of molecules that has similar structure to a query molecule in accordance with the present invention.
Figure 8B:
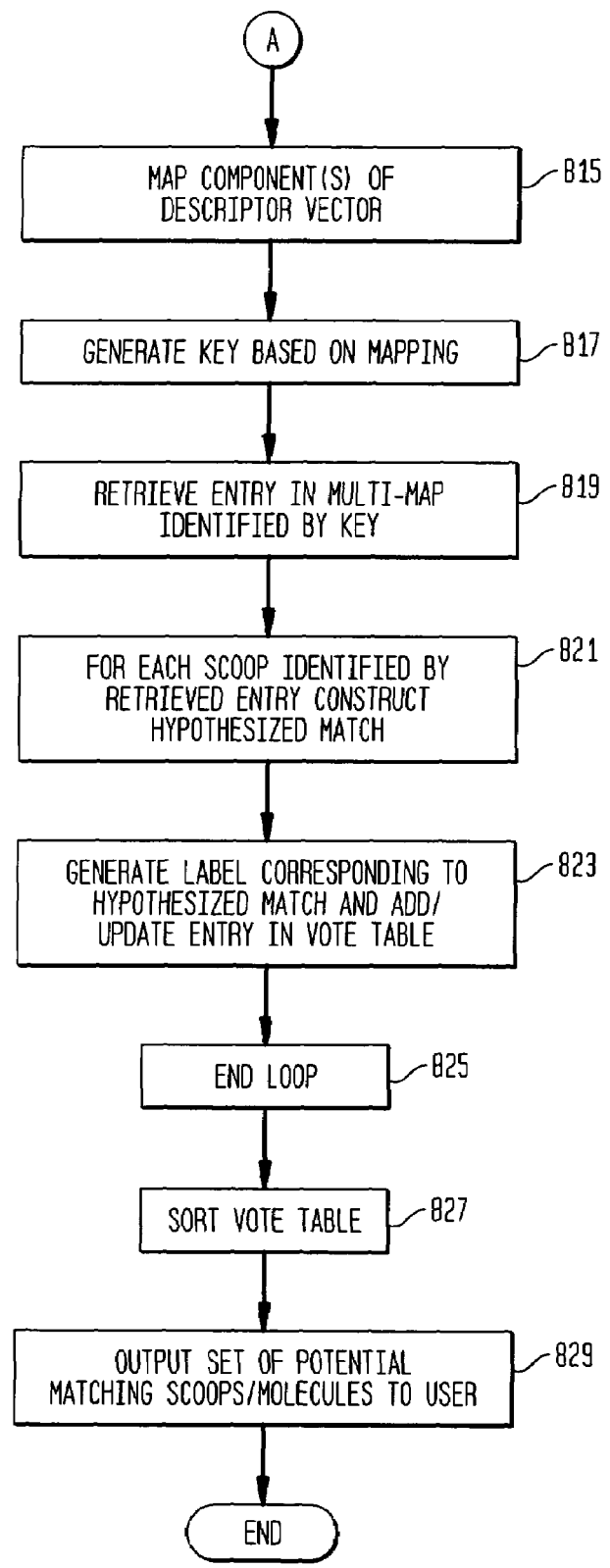

FIGS. 8(A) and (B) illustrates the recognition phase for a query molecule. In step 801, data that represents the structure of the query molecule in the input reference frame is stored in persistent memory. In step 803, data that represents the property distribution of one or more properties of the query molecule is generated, for example by reading such data from persistent memory. The property distribution of the property for a given molecule may be an atomic property distribution, a surface property distribution, or a volumetric property distribution as described above. In step 805, the structure data of the query molecule is used to define a set of scoops (in the input reference frame) in the query molecule. In steps 807-825, a loop is performed over the set of scoops in the query molecule wherein each scoop is processed as follows.

In step 809, the properties of the query molecule that are relevant to the scoop are identified, and the relevant properties are mapped to a property field that represents the value of the property at points in the input reference frame of the query molecule. This operation is similar to the processing described above with respect to step 501 of the training phase.

In step 811, the property field generated in step 809 is mapped to grid points contained in the scoop to determine contribution of property field at the grid points. Preferably, the contribution of property field at a given grid point includes two property values as described above: a positive mass value and a real charge value. This operation is similar to the processing described above with respect to step 503 of the training phase.

In step 813, a descriptive vector for the scoop is generated based upon the property values (mass values and charge values) of the grid points of the scoop generated in step 811. Preferably, the components of the descriptor vector for the scoop includes one or more of the data values as described above with respect to step 505 of the training phase.

In step 815, the mapping generated in step 509 of the training phase is used to map one or more components of the descriptor vector for the scoop generated in step 813 (preferably, the component(s) of the descriptor vector are mapped to a space that optimally discriminates between the groups of scoops as described above with respect to step 217 of FIG. 2). This operation is similar to the processing described above with respect to step 607 of the acquisition phase.

In step 817, a key is generated based upon the mapping of the component(s) of the descriptor vector generated in step 815. The key identifies an entry in the multi-map stored in persistent memory. This operation is similar to the processing described above with respect to step 609 of the acquisition phase.

In step 819, the multi-map entry identified by the key generated in step 817 is retrieved and the data stored therein are read from the retrieved multi-map entry.

Figure 7B:
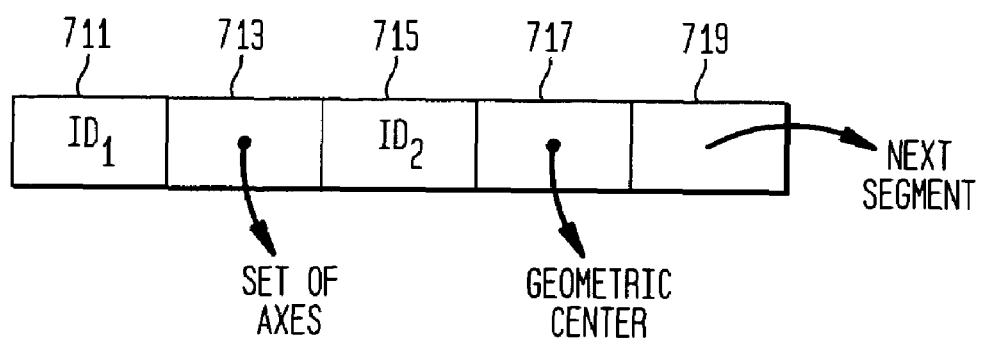

In step 821, for each scoop identified by the retrieved multi-map entry (i.e., each entry segment in FIG. 7), an hypothesized match is constructed to determine a set of transformation parameters whereby a set of axes derived from property distribution of the query scoop is aligned with a set of axes derived from property distribution for each molecular scoop identified by the retrieved multi-map entry, which for the sake of description is referred to below as the stored scoop.

In step 823, a label corresponding to transformation parameters of the hypothesized match is generated, and the hypothesized match is added to a vote table. The vote table is an associative memory of entries keyed by the label. Each entry of the vote table stores i) an accumulated score of the number of stored scoops whose hypothesized match corresponds to the label, and ii) data identifying those stored scoops whose hypothesized match corresponds to the label. Preferably, the vote table is implemented as a map. A detailed description of a map is set forth in D. R. Musser and Atul Saini, STL Tutorial and Reference Guide: C++ Programming with the Standard Template Library (Addison-Wesley 1996), incorporated by reference above in its entirety. The map may be formed from a hash table. A more detailed description of a hash table may be found in R. Sedgewick, Algorithms in C++ (Addison-Wesley 1992), incorporated by reference above in its entirety. In the alternative, the map may be formed from a linked list data structure, or a tree structure such as an AVL-tree or B*tree as described in D. R. Musser and Atul Saini. One skilled in the art will realize that there are many possible underlying implementations for the map data structure.

In step 827, after processing all of the stored scoops identified by the retrieved multi-map entry (step 819), the vote table is sorted to determine a set of potential matching scoops. For example, one or more entries with the highest score may be selected, and those scoops identified by the selected entries of the vote table may be selected as the set of potential matching scoops for the query molecule.

Finally, in step 829, the set of potential matching scoops (and/or the molecules to which the set of potential matching scoops belong) is made accessible to the user, for example, via graphical user interface 907 of the computer processing system.

Figure 9:
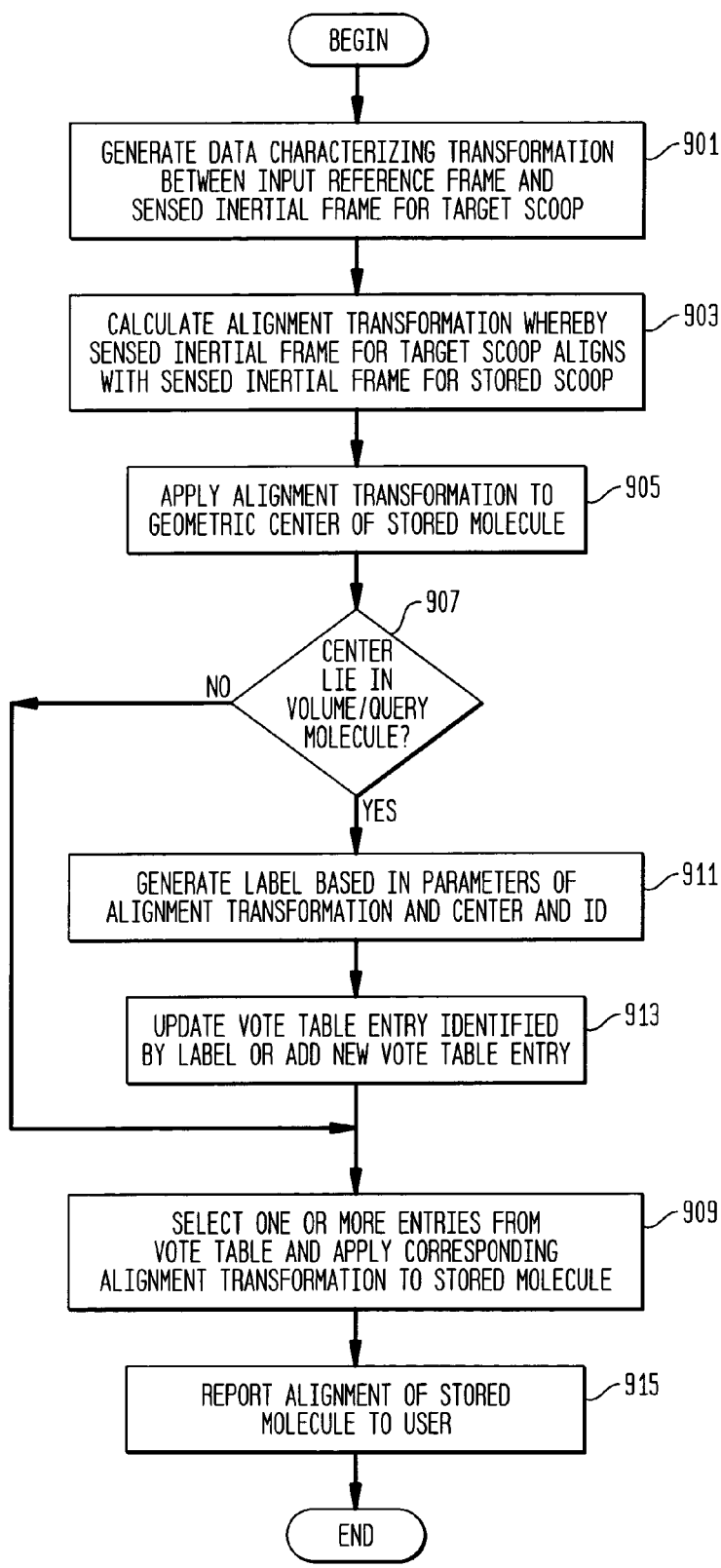
FIG. 9 is a flow chart illustrating an exemplary embodiment of the operations in constructing the match hypothesis in the recognition phase of the present invention.

In the preferred embodiment of the present invention, the operations of the recognition phase in constructing the hypothesized match, adding the hypothesized match to the vote table, and sorting the vote table to report results to the user are illustrated in the flow chart of FIGS. 9(A) and (B). As described above, each entry of the multi-map generated in step 611 of the acquisition phase preferably stores: i) data characterizing transformation between the input reference frame and the sensed inertial reference frame for a given stored scoop—which may include the components $S_x$, $S_y$, $S_z$, $S_\Theta$, $S_\Phi$, $S_{106}$ of the descriptor vector for the stored scoop; ii) data identifying the molecule to which the stored scoop belongs, denoted the stored molecule; and iii) data representing the geometric center in the input reference frame of the stored molecule. Similar operations are performed in the recognition phase in constructing the hypothesized match as illustrated in the flow chart of FIGS. 9(A) and (B).

More specifically, in step 901, data characterizing transformation between the input reference frame and the sensed inertial reference frame for the query scoop—which may include the components $S_x$, $S_y$, $S_z$, $S_\Theta$, $S_\Phi$, $S_\Omega$ of the descriptor vector for the query scoop is generated.

In step 903, data characterizing transformation between the input reference frame for the stored molecule (denoted "stored frame") and the sensed inertial reference frame of the stored scoop ($\hat{u}_1$, $\hat{u}_2$, $\hat{u}_3$ of the stored scoop as described below) and data characterizing transformation between the input reference frame of the query molecule (denoted "query frame") and the sensed inertial reference frame of the query scoop ($\hat{u}_1$, $\hat{u}_2$, $\hat{u}_3$ of the query scoop as described below) are used to calculate a transformation (a translation and rotation transformation) that aligns the two sensed inertial frames, which also represents a transformation from the stored frame to the query frame. Details of an exemplary technique for calculating this transformation may be found in K. Turkowski, "Graphics Gems," Academic Press, edited by A. Glassner, pgs. 522-532, herein incorporated by reference in its entirety.

In step 905, the alignment transformation generated in step 903 is applied to the data representing the geometric center of the stored molecule, which is preferably retrieved from data included in the matching entry of the multi-map, to generate data representing center of the stored molecule in the query frame.

In step 907, it is determined if the center of the stored molecule in the query frame lies within the volume of the query molecule. The volume of the query molecule may be calculated utilizing various well-known techniques, such as the techniques described in Connelly, M. L., "Computation of Molecular Volume," JACS, Vol. 107, 1985, pg. 1118-1124, hereinafter incorporated by reference in its entirety.

If the test of step 907 fails (the center of the stored molecule in the query frame lies outside the volume of the query molecule), in step 909 the construction of the match hypothesis ends without adding an entry to the vote table, and processing continues to step 909

However, if the comparison of step 907 is successful, in step 911 data representing the rotation of the alignment transformation generated in step 903 and data representing center of the stored molecule in the query frame are preferably quantized to form a integer pair, and a label is generated based upon such data and the identifier of the stored molecule.

In step 913, if the vote table does not include an entry corresponding to the label generated in step 911, a new entry associated with the corresponding label is added to the vote table. The new entry includes a score field with an initial value (for example, 1), data identifying the given stored scoop, and data identifying the alignment transformation generated in step 903. Otherwise (the vote table does not include an entry corresponding to the label generated in step 911), the score field of the corresponding entry is incremented and possibly data identifying the stored scoop is added to the entry. In addition, the alignment transformation data may be updated, for example, to represent the cumulative average alignment transformation. The operation then continue to step 909.

In step 909, one or more entries of the vote table is selected, and the alignment transformation corresponding to the selected entry (ies) is applied to the corresponding stored molecule (which is identified by the label associated with the vote table entry) to generate an alignment of the stored molecule in the query frame.

Finally, in step 915, the alignment of the stored molecule in the query frame is reported to the user via an I/O device and operation of the recognition phase ends.

It should be noted that the operations described above with respect to FIG. 9 represent a preferred embodiment of the present invention. One skilled in the art will realize that the operations similar to those described above can be used to construct an hypothesized match between a stored scoop and a query scoop based upon any data characterizing a set of axes derived from the property distribution of the stored scoop and query scoop, respectively.

As described above, the training phase is used to define the association criteria between query scoops and stored scoops, and keys and the corresponding multi-map data structure capture the associations. In an alternate embodiment, any arbitrary selection scheme (for example, one based on a distance metric) can be used to associate a query scoop with a stored scoop, which leads to construction of a match hypothesis between the query scoop and the associated stored scoop.

Figure 1B:
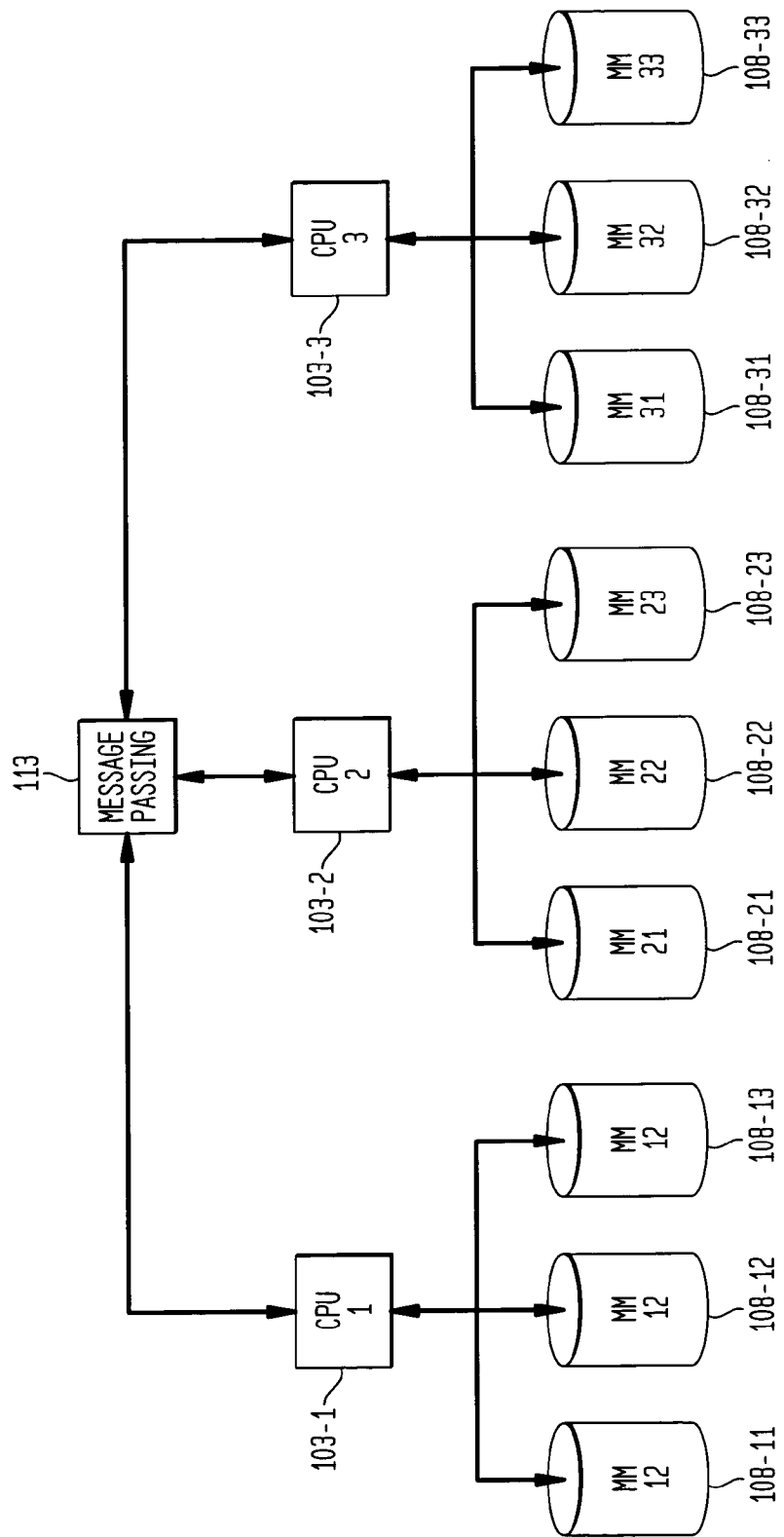

The computer processing system 100 that implements the present invention may be distributed in nature as shown in FIG. 1(B). More specifically, a distributed computer processing system comprises more than one CPU 103 (three shown 103-1, 103-2, 103-3) with each of these CPUs communicating with one another via message passing utility 113. The message passing utility 113 may be implemented via shared memory, a network connection, a high speed switch or some other method that allows data to be passed from CPU to CPU. A distributed computer processing system is preferably used for the recognition phase of the present invention because of the inherently parallel nature of the algorithm. More specifically, the multi-map data structure generated in the acquisition mode as described below is preferably partitioned amongst the CPUs of the distributed system. The multi-map data structure may also be partitioned amongst the various nonvolatile storage devices 108 associated with a given CPU 103. For example, the multi-map may be partitioned into nine portions MM11, MM12, MM13, MM21, MM22, MM23, MM31, MM32, MM33 among three CPUs 103-1, 103-2 and 103-3 and their associated nine storage devices 108-11, 108-12, 108-13, 108-21,1 08-22, 108-23, 108-31, 108-32, 108-33 as shown. In addition, the vote table data structure may be similarly partitioned amongst the CPUs of the distributed system. When such a system is used in the recognition phase described above, as table entries are retrieved from the multi-map, such table entries are routed via the message passing utility 113 to the appropriate CPU for accumulation in the proper segment of the vote table. In the end, a distributed merge sort is preferably used to collate all of the resulting hypothesized matches on a single CPU.

Derivation of Components of Descriptor Vectors for a Scoop

As described above, the components of the descriptor vector characterizing a given scoop preferably includes $S_x$, $S_y$, $S_z$, which represent the components of a vector describing translation between the origin of input reference frame and center of mass in the input reference frame. These components may be calculated utilizing well know techniques, including the operations described in column 6 of U.S. Pat. No. 5,784,294 to Platt et al., incorporated by reference above in its entirety.

In addition, the components of the descriptor vector characterizing a given scoop preferably includes the principal values of the moment of inertia tensor I for the scoop, which are denoted $I_x$, $I_y$, $I_z$. The inertial reference frame for the scoop is preferably characterized by an origin at the center of mass in the input reference frame, and a set of three axes (denoted $\hat{u}_1$, $\hat{u}_2$, $\hat{u}_3$) in the input reference frame. The axes $\hat{u}_1$, $\hat{u}_2$, $\hat{u}_3$ are unit vectors that point in the same direction as corresponding eigenvectors (principal axes) of the diagonalized moment of inertia tensor I of the scoop. The principal values of the moment of inertia tensor I of the scoop ($I_x$, $I_y$, $I_z$) are represented by the eigenvalues of the diagonalized moment of inertia tensor I of the scoop. The eigenvectors (principal axes) and the corresponding eigenvalues of the diagonalized moment of inertia tensor I for the scoop may be calculated utilizing the operations described in columns 6-8 of U.S. Pat. No. 5,784,294 to Platt et al., incorporated by reference above in its entirety.

Importantly, the three axes $\hat{u}_1$, $\hat{u}_2$, $\hat{u}_3$ do not sufficiently denote an internal frame of reference for coordinate transformation because the signs of the corresponding eigenvectors are ambiguous. The signs must be determined from other information.

Accordingly, the present invention provides a procedure for sensing the axes $\hat{u}_1$, $\hat{u}_2$, $\hat{u}_3$ with a third order moment vector, which is denoted the asymmetric vector, in order to denote an internal frame of reference sufficient for coordinate transformation. The asymmetric vector has a general form $\vec{C}=(C_x, C_y, C_z)$. This general form may characterize a third order moment of mass about a center of expansion, denoted above as $\vec{C}_i=(Ci_x, Ci_y, Ci_z)$. In the alternative, the general form may characterize a third order moment of charge about center of expansion, denoted above as $\vec{C}_q=(Cq_x, Cq_y, Cq_z)$.

In the preferred embodiment of the present invention, the components of the asymmetric vector $\vec{C}=(C_x, C_y, C_z)$ are derived as follows:

$$\vec{C} = \int p(\vec{x}) |\vec{x}|^2 \vec{x}\, d^3x$$

where $\vec{x}$ represents a vector between the center of expansion and any arbitrary point in the input reference frame, and $p(\vec{x})$ represents the relevant distribution (i.e., represent the mass distribution for the asymmetric vector characterizing third order moment of mass, or represents the charge distribution for asymmetric vector characterizing third order moment of charge) of the scoop at points in the input reference frame corresponding to the vector $\vec{x}$.

In systems where the distribution $p(\vec{x})$ of the scoop has discrete values over points in the input reference frame, the components of the asymmetric vector $\vec{C}=(C_x, C_y, C_z)$ may be derived as follows:

$$\vec{C} = \Sigma p_i |\vec{x}_i|^2 \vec{x}_i$$

where $\vec{x}_i$ represents a vector between the center of expansion in the input reference frame and a grid point i in the input reference frame, $p_i$ is the mass/charge property at the grid point i (when generating the asymmetric vector characterizing the third order moment of mass, $p_i$ is the mass value $\mu_i$ for the grid point i as described above with respect to step 503; and when generating the asymmetric vector characterizing third order moment of charge, $p_i$ is the charge value $\chi_i$ for the gird point i as described above with respect to step 503); and $\Sigma$ sums over the grid points of the scoop.

With respect to the asymmetric vector $\vec{C}_i$ characterizing third order moment of mass for the scoop, preferably the center of expansion is the center of mass of the scoop. With respect to the asymmetric vector $\vec{C}_q$ characterizing third order moment of charge for the scoop, the center of expansion may be the center of charge, center of dipole, or center of quadrupole for the scoop.

As described above, the components of asymmetric vector $\vec{C}$ (such as the asymmetric vector $\vec{C}_i$ characterizing third order moment of mass for the scoop, or the asymmetric vector $\vec{C}_q$ characterizing third order moment of charge for the scoop) are used to sense the axes $\hat{u}_1$, $\hat{u}_2$, $\hat{u}_3$ in order to denote an internal frame of reference sufficient for coordinate transformation. Preferably, the axes $\hat{u}_1$, $\hat{u}_2$, $\hat{u}_3$ are sensed by looping over a counter y ranging from 1 to 2 with an increment of 1. In each iteration of the loop, the following conditional operation is performed: if the dot product of the axis $\hat{u}_{[y]}$ and the asymmetric vector is less than zero, then the sign of $\hat{u}_{[y]}$ is swapped (i.e., $\hat{u}_{[y]}=-\hat{u}_{[y]}$). In the first iteration of the loop, the counter y is 1 and the conditional operation tests whether the dot product of the axis $\hat{u}_1$ and the asymmetric vector is less than zero. If so, the sign of $\hat{u}_1$ is swapped. Otherwise, the sign of $\hat{u}_1$ remains uncharged. In the second iteration of the loop, the counter y is 2 and the conditional operation tests whether the dot product of the axis $\hat{u}_2$ and the asymmetric is less than zero. If so, the sign of $\hat{u}_2$ is swapped. Otherwise, the sign of $\hat{u}_2$ remains uncharged. The loop then terminates, and the third axis $\hat{u}_3$ is constructed as the cross product of $\hat{u}_1$ and $\hat{u}_2$.

Importantly, the sensed axes $\hat{u}_1$, $\hat{u}_2$, $\hat{u}_3$ denote a reference frame suitable for coordinate transformation. More specifically, this reference frame is characterized by an origin at the center of mass in the input reference frame, and the sensed axes ($\hat{u}_1$, $\hat{u}_2$, $\hat{u}_3$ in the input reference frame). This reference frame is preferably used to generate components of the descriptor vector that characterizes a scoop.

In addition, the components of the descriptor vector characterizing a given scoop includes the components of a transformation matrix representing rotation between the principal axes of moment of inertia tensor I for the scoop and the axes of input reference frame. Preferably, this transformation matrix, which for the sake of description is denoted R, is derived from the sensed axes $\hat{u}_1(=\mu_{1x}\hat{x}+\mu_{1y}\hat{y}+\mu_{1z}\hat{z})$, $\hat{u}_2(=\mu_{2x}\hat{x}+\mu_{2y}\hat{y}+\mu_{2z}\hat{z})$, and $\hat{u}_3(=\mu_{3x}\hat{x}+\mu_{3y}\hat{y}+\mu_{3z}\hat{z})$ as follows:

$$R = \begin{matrix} u_{1x} & u_{1y} & u_{1z} \\ u_{2x} & u_{2y} & u_{2z} \\ u_{3x} & u_{3y} & u_{3z} \end{matrix}$$

Note that this representation has nine terms. Preferably, the transformation matrix R may be represented by three angles: $S_\Theta$, $S_\Phi$, $S_\Omega$. $S_\Phi$, $S_\Theta$ are polar angles that describe an axis of rotation. $S_\Omega$ represents an angle of rotation about that angle. Together, the angles represent the rotation transformation represented by the transformation matrix R. The rotation matrix R and the angles $S_\Theta$, $S_\Phi$, $S_\Omega$ can be calculated using the technique described in M. Pique, "Graphics Gems," Academic Press, edited by A. Glassner, pgs. 465-467, herein incorporated by reference in its entirety. Note that this representation of the rotation transformation using the angles $S_\Theta$, $S_\Phi$, $S_\Omega$ only has three terms, which is advantageous because it lowers the storage allocation requirements for the components of the descriptor vector of the scoop that represent the transformation.

In addition, the components of the descriptor vector characterizing a given scoop preferably includes the components of a vector describing translation between center of scoop in the inertial reference frame and center of mass in the inertial reference frame, which are denoted $v_x$, $v_y$, $v_z$. Preferably, the components $v_x$, $v_y$, and $v_z$ are derived by generating a vector representing translation between center of scoop in the input reference frame and center of mass in the input reference frame, and then applying the rotation transformation matrix R described above to transform the vector from the input reference frame to the inertial reference frame represented by the sensed axes $\hat{u}_1$, $\hat{u}_2$, $\hat{u}_3$.

In addition, the components of the descriptor vector characterizing a given scoop preferably includes the components of a vector describing translation between center of mass in the inertial reference frame and center of dipole in the inertial reference frame, which are denoted $d_x$, $d_y$, $d_z$. Preferably, the components $d_x$, $d_y$, and $d_z$ are derived by generating a vector representing translation between center of mass in the input reference frame and center of dipole mass in the input reference frame, and then applying the rotation transformation matrix R described above to transform the vector from the input reference frame to the inertial reference frame represented by the sensed axes $\hat{u}_1$, $\hat{u}_2$, $\hat{u}_3$. The center of dipole in the inertial reference frame may calculated utilizing the operations described in columns 10-11 of U.S. Pat. No. 5,784,294 to Platt et. al., incorporated by reference above in its entirety.

In addition, the components of the descriptor vector characterizing a given scoop preferably includes one or more components of a tensor characterizing the quadrupolar moment about a center of expansion, which are denoted $Q_{xx}$, $Q_{xy}$, $Q_{xz}$, $Q_{yz}$, $Q_{zz}$. Preferably, the components $Q_{xx}$, $Q_{xy}$, $Q_{xz}$, $Q_{yy}$, $Q_{yz}$, $Q_{zz}$ characterize contribution of such quadrupolar moment along the sensed axes $\hat{u}_1$, $\hat{u}_2$, $\hat{u}_3$. In this case, components of a tensor Q characterizing quadrupolar moment about a center of expansion are generated. The components of the tensor Q may be calculated utilizing the operations described in columns 10-11 of U.S. Pat. No. 5,784,294 to Platt et. al., incorporated by reference above in its entirely. Finally, the following operations are performed with respect to the tensor Q to calculate contribution of the tensor Q along the sensed axes $\hat{u}_1$, $\hat{u}_2$, $\hat{u}_3$:

$Q_{xx}=\hat{u}_1 \cdot Q \cdot \hat{u}_1$
$Q_{xy}=\hat{u}_1 \cdot Q \cdot \hat{u}_2$
$Q_{xz}=\hat{u}_1 \cdot Q \cdot \hat{u}_3$
$Q_{yy}=\hat{u}_2 \cdot Q \cdot \hat{u}_2$
$Q_{yz}=\hat{u}_2 \cdot Q \cdot \hat{u}_3$
$Q_{zz}=\hat{u}_3 \cdot Q \cdot \hat{u}_3$ While the invention has been described in connection with specific embodiments, it will be understood that those with skill in the art may develop variations of the disclosed embodiments without departing from the spirit and scope of the following claims.

We claim:

1. A method implemented in a data processing system for generating and storing data characterizing at least one region of said plurality of regions, wherein the data process system comprising a plurality of descriptor vectors associated with a plurality of regions of molecules stored in a database, wherein the plurality of descriptor vectors are classified into groups, the method comprising the steps of:

generating an entry comprising i) an identifier that identifies said at least one region, and ii) data characterizing a set of axes derived from a property distribution of said at least one region;

mapping a descriptor vector associated with said at least one region based on preselected criteria, wherein the mapping maps said plurality of descriptor vectors to a space discriminating between said groups of descriptor vectors;

wherein said mapping is derived from the steps of:
generating first data representing differences between said groups of descriptor vectors;
generating second data representing variations within said groups of descriptor vectors;
identifying a set of component vectors that maximizes an F disturbed criterion function, said F distributed criterion function having a numerator based upon said first data and a denominator based upon said second data;
generating an F distributed statistic for subsets of said component vectors, said F distributed statistic having a numerator based upon said first data and a denominator based upon said second data;
for each particular subset of component vectors, calculating a probability value for the F-distributed statistic associated with the particular subset;
selecting a probability value from probability values for said subsets of component vectors based upon a predetermined criterion;
identifying the subset of said component vectors associated with the selected probability value;
generating a mapping to a space corresponding to the subset of component vectors associated with the selected probability value, and storing the mapping for subsequent processing;

generating a key that corresponds to said mapping of the descriptor vector associated with said at least one region; and storing said entry in a memory, wherein said key is associated with said entry such that the key indexes the entry for retrieval.

2. The method of claim 1, wherein said property distribution of said at least one region is computed from a convolution with a probe function to a property field.

3. The method of claim 1, wherein said first data comprises a matrix $\epsilon_b$ representing covariance between said groups of descriptor vectors, and said second data comprises a matrix $\epsilon_w$ representing covariance within said groups of descriptor vectors.

4. The method of claim 3, wherein said criterion function has the general form:

$$f(\hat{w}) = C\left(\frac{\hat{w}^T \varepsilon_b \hat{w}}{\hat{w}^T \varepsilon_w \hat{w}}\right)$$

where $\hat{w}$ is some vector, T indicates a transpose, $\epsilon_b$ is a first data representing covariance, $\epsilon_w$ is a second data representing covariance and C is a constant based upon degrees of freedom in $\epsilon_b$ and $\epsilon_w$.

5. The method of claim 4, wherein C is determined as follows:

$$C = \frac{1/\text{degrees of freedom in } \varepsilon_b}{1/\text{degrees of freedom in } \varepsilon_w} = \frac{1/(N-1)}{1/(\sum n_i - N)}$$

where N represents the number of groups of descriptor vectors, $n_i$ represents the number of regions, and $\Sigma n_i$ represents the sum of $n_i$ for the N groups.

6. The method of claim 3, wherein the step of identifying a set of component vectors that maximizes an F distributed criterion function comprises the substeps of:
determining a set of (eigenvalue, eigenvector) pairs for the matrix $\epsilon_w$
determining said set of component vectors based upon said set of (eigenvalue, eigenvector) pairs for the matrix $\epsilon_w$.

7. The method of claim 6, wherein said statistic for a given subset of component vectors is based upon value of said criterion function for said subset of component vectors.

8. The method of claim 7, wherein said statistic for a given subset of component vectors has the following form:

$$\Psi_s = C\left(\frac{1}{L_S}\right)\sum f_k$$

where
$f_k$ represents the value of the criterion function at a component vector in the given subset,
C is a constant,
$L_S$ represents the number of $f_k$ values in the given subset of component vectors, and
the $\Sigma$ operation sums over the $L_S$ $f_k$ values in the given subset of component vectors.

9. The method of claim 8, wherein said a probability value for a particular F-distributed statistic represents a probability value that the particular F-distributed statistic could have been larger by chance.

10. The method of claim 9, wherein said probability value selected from probability values for said subsets of component vectors is a minimum probability value of said probability values for said subsets of component vectors.

11. The method of claim 1, wherein said mapping for said at least one descriptor vector performs a loop over each component vector belonging to the subset of component vectors associated with the selected probability; wherein, in each iteration of said loop, dot product of said descriptor vector with a transpose of a unit vector for the given component vector is added to a running sum.

12. The method of claim 1, wherein at least one descriptor vector is invariant to rotation and translation of the at least one region.

13. The method of claim 12, wherein the set of axes is derived from principal axes of second moments of a region of the property distribution information.

14. The method of claim 1, wherein the probability value is obtained by treating the ratio as an F-distributed statistic.

* * * * *

UNITED STATES PATENT AND TRADEMARK OFFICE
CERTIFICATE OF CORRECTION

| | | |
|---|---|---|
| PATENT NO. | : 7,356,415 B1 | |
| APPLICATION NO. | : 09/275568 | |
| DATED | : April 8, 2008 | |
| INVENTOR(S) | : Michael C. Pitman and Daniel E. Platt | |

It is certified that error appears in the above-identified patent and that said Letters Patent is hereby corrected as shown below:

Claim 1 at Col. 28, line 45, should say:

"an F distributed criterion function, said F distributed" and --not-- an F disturbed criterion function, said F distributed

Please change the word "disturbed" in claim 1 to "distributed."

Signed and Sealed this
Twenty-eighth Day of June, 2011

David J. Kappos
*Director of the United States Patent and Trademark Office*